United States Patent [19]

Wrighton

[11] Patent Number: 4,936,956
[45] Date of Patent: Jun. 26, 1990

[54] MICROELECTROCHEMICAL DEVICES BASED ON INORGANIC REDOX ACTIVE MATERIAL AND METHOD FOR SENSING

[75] Inventor: Mark S. Wrighton, Winchester, Mass.

[73] Assignee: Massachusetts Institute of Technology, Cambridge, Mass.

[21] Appl. No.: 114,566

[22] Filed: Oct. 29, 1987

Related U.S. Application Data

[63] Continuation-in-part of Ser. No. 674,410, Nov. 23, 1984, Pat. No. 4,721,601.

[51] Int. Cl.[5] ............................................. G01N 27/46
[52] U.S. Cl. .............................. 204/153.21; 204/403; 204/415; 204/419; 204/433; 357/25
[58] Field of Search .............. 204/1 T, 403, 412, 415, 204/416, 418, 419, 433, 435, 420; 357/25; 324/71.5; 435/817

[56] References Cited

U.S. PATENT DOCUMENTS

| | | | |
|---|---|---|---|
| 4,020,830 | 5/1977 | Johnson et al. | 204/412 X |
| 4,103,227 | 7/1978 | Zemel | 357/25 X |
| 4,305,802 | 12/1981 | Koshiishi | 357/25 X |
| 4,354,308 | 10/1982 | Shimada et al. | 357/25 X |
| 4,411,741 | 10/1983 | Janata | 204/412 X |
| 4,502,938 | 3/1985 | Covington et al. | 204/412 X |
| 4,505,799 | 3/1985 | Baxter | 204/416 |
| 4,613,422 | 9/1986 | Lauks | 204/416 X |
| 4,739,380 | 4/1988 | Lauks et al. | 357/25 |

OTHER PUBLICATIONS

S. M. Sze, "VLSI Technology", McGraw-Hill Book Co., 1983, p. 468–471.
Thackeray, James W. and Mark S. Wrighton, "Chemically Responsive Microelectrochemical Devices Based on Plantinized Poly (3-methylthiophene): Variation in Conductivity with Variation in Hydrogen, Oxygen, or pH in Aqueous Solution," 90 J. Phys. Chem., 6674–79 (1986).
Natan, Michael J., Thomas E. Mallouk, and Mark S. Wrighton, "pH-Sensitive $WO_3$-Based Microelectrochemical Transistors," 91 J. Phys. Chem. 648–54 (1987).
Natan, Michael J., Daniel Belanger, Michael K. Carpenter, and Mark S. Wrighton, "pH-Sensitive $Ni(OH)_2$-Based Microelectrochemical Transistors," 91 J. Phys. Chem. 1834–42 (1987).
Chao, Shuchi and Mark S. Wrighton, "Solid-State Microelectrochemistry: Electrical Characteristics of a Solid-State Microelectrochemical Transistor Based on Poly (3-methylthiophene)," 109 J. Am. Chem. Soc. 2197–9 (1987).
Lyons, Donald J., Martin O. Schlon, James J. Hickman, and Mark S. Wrighton, "Ruthenium Oxide-Based Microelectrochemical Devices: Electrochemical Behavior of the Oxide Formed by Reduction of $RuO_4^{2-}$." (submitted to J. Phys. Chem. as of 12/87).

Primary Examiner—Nam X. Nguyen
Attorney, Agent, or Firm—Kilpatrick & Cody

[57] ABSTRACT

Novel microelectrochemical devices are provided which consist of closely spaced microelectrodes coated with metal ion based inorganic redox active material such as oxides or mixed oxides of any of the following transition metals: W, Ni, Ru, Co, Rh, Ir, Nb, Mo, V, or any other metal that undergoes a change in electrical conductivity upon electrochemical oxidation or reduction, in contact with an electrolyte. Additionally, other metal based redox materials whose conductivity changes as a function of the movement of ions into or out of the material can be used in the construction of microelectronic devices, for example, Prussian Blue, $Fe_4[Fe(CH)_6]_3$.

"Metal ion-based microelectrochemical devices" encompasses all devices based on an inorganic redox active material which incorporate an active "gate" region or "channel", or exhibit rectification. Included in this classification are devices analogous to diodes, field effect transistors, p-n-p transistors, and n-p-n transistors, and pH sensors, among others. A number of specific examples of transistors and sensors are described in detail.

22 Claims, 16 Drawing Sheets (a) As Fabricated
(b) Au Shadowed
(c) SiO$_2$ Shadowed
(d) Polymer Modified

SHADOW DEPOSITION

4,936,956

MICROELECTROCHEMICAL DEVICES BASED ON INORGANIC REDOX ACTIVE MATERIAL AND METHOD FOR SENSING

The United States Government has certain rights in this invention by virtue of Defense Advanced Research Project Agency grant No. N00014-84-K-0291 and Office of Naval Research grant No. N00014-84-K-0553.

This application is a continuation in part of U.S. Ser. No. 674,410 filed Nov. 23, 1984 by Mark S. Wrighton, Henry S. White and Gregg P. Kittlesen entitled "Molecule-Based Microelectronic Devices" issued Jan. 26, 1988 as U.S. Pat. No. 4,721,601.

BACKGROUND OF THE INVENTION

The present invention is in the general area of microelectrochemical devices and particularly relates to devices based on inorganic redox active material.

U.S. Pat. No. 4,721,601 discloses several types of novel microelectrochemical devices analogous to diodes, transistors, sensors, surface energy storage elements and light emitting devices which are formed from microelectrodes overlaid with electrochemically polymerizable redox materials. The physical properties of these materials change in response to a chemical or electrical signal altering the concentration of ionic species in the polymer. Examples of the redox polymers include polypyrrole, polyaniline, polythiophene, and other materials that are conducting when oxidized and insulating when reduced. Crucial to the practical application of most of these devices is the close spacing between electrodes, on the order of less than two microns, since the response time and sensitivity of the device depend on the spacing between electrodes as well as on the polymer selection.

Despite the tremendous potential and variety of applications made possible by the devices disclosed in U.S. Pat. No. 4,721,601 there remains a need for devices made with materials which transmit signals under different conditions (for example, when the redox material is reduced, rather than oxidized), which are more stable at extremes of pH or other environmental conditions, and which are sensitive to specific chemical signals.

It is therefore an object of the present invention to provide novel microelectrochemical devices formed with inorganic redox materials.

It is a further object of the present invention to provide such microelectrochemical devices exhibiting a reproducible proportional change in current as a function of pH or other specific chemical input.

It is still another object of the present invention to provide microelectrochemical devices which are stable in very basic electrolyte solutions and at other environmental extremes.

SUMMARY OF THE INVENTION

Novel microelectrochemical devices are provided which consist of closely spaced microelectrodes coated with inorganic redox active materials such as oxides or mixed oxides of any of the following transition metals: W, Ni, Ru, Co, Rh, Ir, Nb, Mo, V, or any other metal that undergoes a change in electrical conductivity upon electrochemical oxidation or reduction, in contact with an electrolyte. Additionally, other metal based redox materials whose conductivity changes as a function of the movement of ions into or out of the material can be used in the construction of microelectronic devices, for example, Prussian Blue, $Fe_4[Fe(CN)_6]_3$.

"Metal ion-based microelectrochemical devices" encompasses all devices based on an inorganic redox active material which incorporate an active "gate" region or "channel", or exhibit rectification. Included in this classification are devices analogous to diodes, field effect transistors, p-n-p transistors, and n-p-n transistors, and pH sensors, among others. Specific examples of transistors and sensors are described.

The device microelectrodes are preferably fabricated and patterned by photolithographic techniques. The redox material is then deposited on the microelectrodes with sufficient thickness to establish electrical contact between adjacent microelectrodes. The redox material may be deposited electrochemically, by rf plasma deposition, sputtering or e-beam deposition, or by spray pyrolysis of appropriate organometallics. Alternatively, oxide-coated microelectrodes can be prepared by thermal oxidation of transition metal-coated microelectrodes.

Modifications include incorporation of metals into the oxide layer or onto the surface contacting the electrolyte, covalent attachment of molecules or polymers to functionalities native to the oxide or to chemically prepared functionalities, and establishment of electrical contact with other materials, such as other oxides or redox polymers, on adjacent microelectrodes or microelectrochemical devices.

DETAILED DESCRIPTION OF THE INVENTION

Using one or more redox materials as the active element in microelectronic devices provides a means for constructing unique devices having new functions. Since many redox materials are intrinsically chemically sensitive, the new microelectronic devices represent a novel class of chemical sensors that are specific, sensitive, and small. Surface modification of these microfabricated structures finds application in interfacing microelectronics with biological systems, owing to the need to make surfaces "biocompatible".

Figure 1:
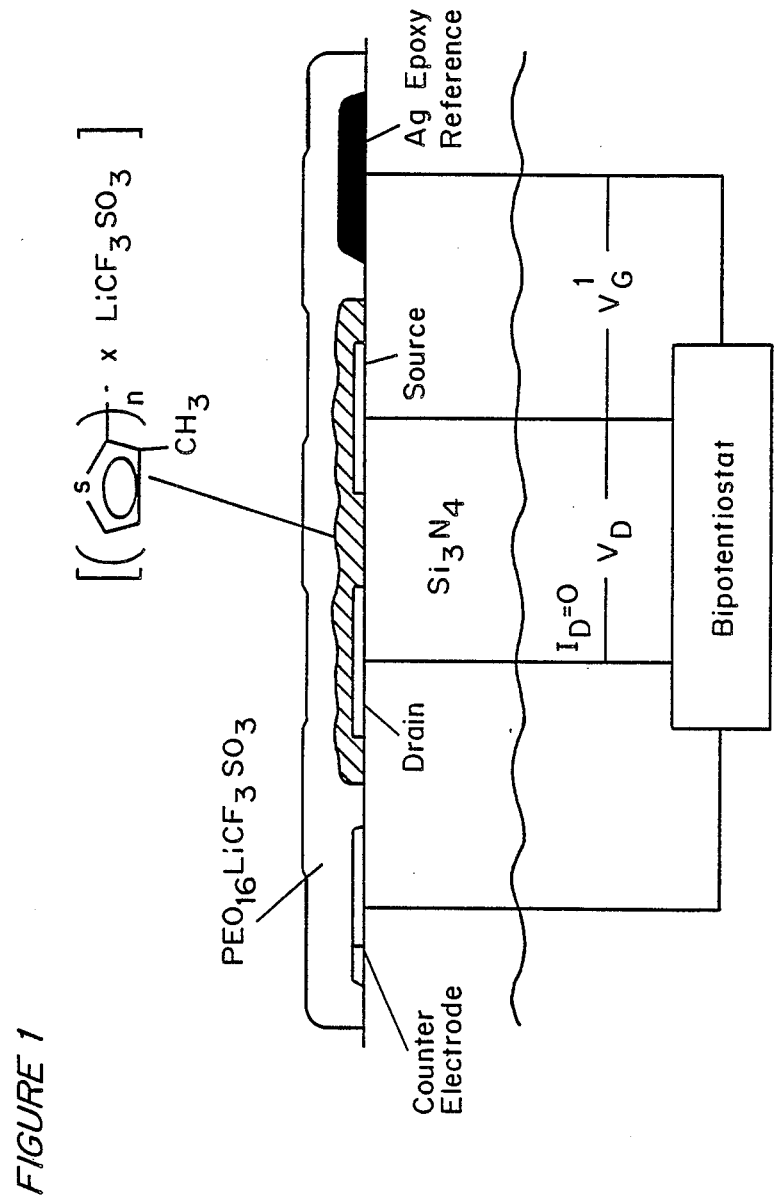
FIG. 1 is a cross sectional view of a redox polymer-based microelectrode transistor, where the polymer is poly(3-methylthiophene) and the reference electrode is Ag-epoxy, in its "off" state, as described in the parent application.

FIG. 1 illustrates a cross-sectional view of a microelectrochemical transistor where the active material is a redox active material, an organic polymer, poly(3-methylthiophene), which connects two microelectrodes analogous to the source and drain of a conventional transistor. The essential property of the redox material is that its "conductivity" is a function of its state of charge, which can be controlled through the gate potential, $V_G$. Thus, upon variation in $V_G$, there is a change in the drain current, $I_D$, for a fixed potential between source and drain, $V_D$, as in a solid state transistor.

All redox materials can be used to make a microelectrochemical transistor. Further, many redox materials can be expected to have a chemically sensitive "conductivity" and a chemically sensitive potential for maximum conductivity. Thus, connecting two electrodes with a single redox material results in a device having electrical characteristics dependent on the medium to which it is exposed.

A small spacing between the source and drain is crucial to maintain a small $I_D$ for a microelectrochemical transistor as represented by FIG. 1. In fact, so many redox materials have such poor conductivity at any $V_G$ that measurable values of $I_D$ require spacings as small as possible. Further, since the spacing between source and drain also defines the switching speed, or response time, of the device, smaller spacings yeild faster switching.

Figure 2:
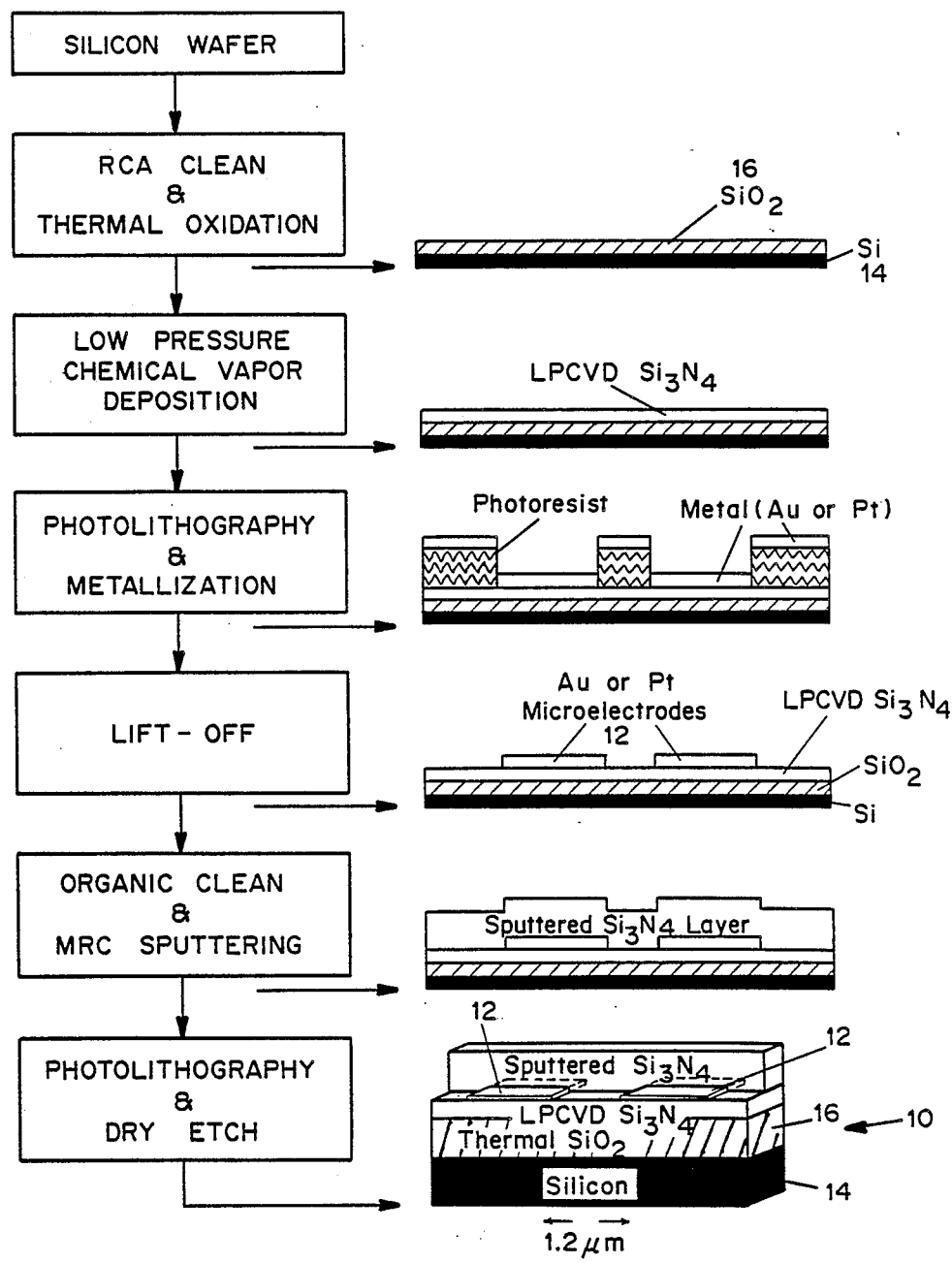
FIG. 2 is a flow chart for fabrication of microelectrode arrays using photolithographic techniques, as described in detail in the parent application.

The technology for constructing devices having small separations is available. FIG. 2 diagrams the fabrication of a microelectrode array 10 consisting of individually addressable gold or platinum microelectrodes 12 each $\approx 2.5$ μm wide x $\approx 50$ μm long x $\approx 0.1$ μm high, separated from each other by $\approx 1.5$ μm, as described in U.S. Pat. No. 4,721,601. As diagrammed, a device is constructed by providing a silicon wafer 14 overlaid with a SiO$_2$ layer 16 produced by thermal oxidation, overlaid with Si$_3$N$_4$ by low pressure chemical vapor deposition, patterning and depositing the microelectrodes 12 using photolithography and metallization techniques known to those skilled in the art and 11 cleaning (for example, by organic solution, MRC sputtering, and dry etching).

Figure 3B:
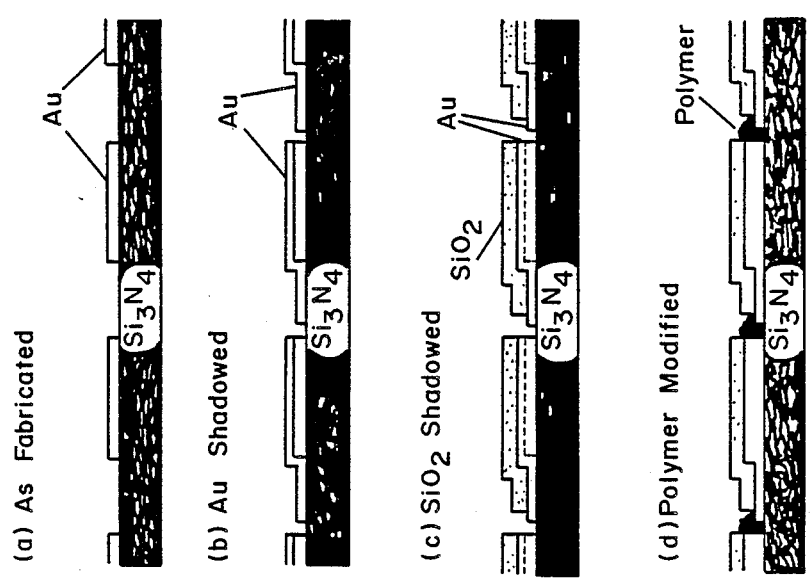
FIGS. 3a to 3b are a flow chart for fabrication of microelectrode arrays using shadow deposition techniques.
Figure 3A:
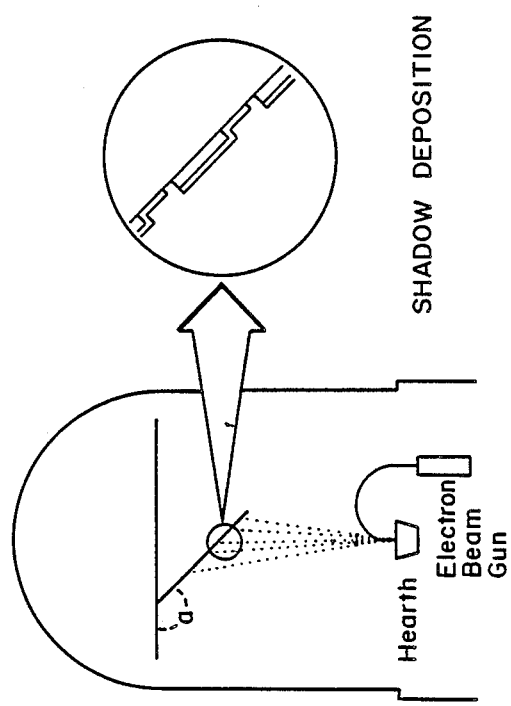

FIG. 3 diagrams a "shadow deposition" method as described by E. T. Jones, O. M. Chyan, and M. S. Wrighton entitled "Preparation and Characterization of Molecule-Based Transistors with a 50 Nanonmeter Source-Drain Separation Using Shadow Deposition Techniques: Towards Faster, More Sensitive Molecule-Based Devices" in *J.Amer.Chem.Soc.* (in press, 1987). As used according to the present invention a device with a significantly smaller spacing between microelectrodes, on the order of 50 nm, can be produced. The procedure begins with a Si$_3$N$_4$-coated Si wafer of microelectrode arrays of eight, individually addressable gold microelectrodes each 50 microns long $\times 2.5$ microns wide$\times 0.1$ microns thick with spacings between microelectrodes of 1.5 microns. The first step involves a line of sight e$^-$beam deposition of 50 nm of gold onto the wafer at an angle, closing the spacing to 50 to 100 nm as established by scanning electron microscopy (SEM). A second shadow deposition process, line of sight e$^-$ beam deposition of 100 nm of SiO$_2$ at an angle smaller than for the gold deposition step, covers the majority of the exposed gold with an insulator. The result is a set of closely-spaced (50–100 nm) microelectrodes with ultrasmall electrode areas. The total microelectrode area is estimated to be below $10^{-7}$ cm$^2$ per microelectrode.

In conventional redox materials, the mechanism for charge transport in the polymer relies on self-exchange from one redox site to another. That is, when there is a concentration gradient of oxidized and reduced centers, there can be a steady state current that depends on the diffusion coefficient for charge transport, $D_{c\,t}$, in the redox material; the distance across which the charge is transported, d; and the concentration of redox centers in the redox material, C:

$$I_{D(max)} = \frac{nFAD_{ct}C}{d} \quad (1)$$

where n is the number of electrons transferred, F is the faraday, and A is the electrode area through which charge passes. $I_{D(max)}$ refers to the maximum current possible, which occurs at the maximum concentration gradient of oxidized and reduced sites. $D_{ct}$ from hydrolysis of the Si-OMe bonds of a viologen-based redox polymer is $\approx 10^{-9}$ cm$^2$/s and C is $\approx 2.5$ M. A value of d=1.0 μm gives a maximum drain current density of $\approx 2$ mA/cm$^2$. According to equation (1), $I_{D(max)}$ is inversely proportional to d, which underscores the importance of small spacings.

Many redox active polymers can undergo dramatic changes, up to greater than eight orders of magnitude, in conductivity depending on their state of charge. Such materials, including polypyrrole, poly(N-methylpyrrole), poly(3-methylthiophene) and polyaniline, have been used in the construction of the first microelectrochemical devices, described in U.S. Pat. No. 4,721,601.

The high absolute conductivity of conducting redox polymers, their good reversibility in terms of switching between their insulating and conducting states, and the ability to selectively deposit them by electrochemical methods make conducting polymers good candidates for the active material in microelectrochemical transistors.

Modification of microelectrode arrays with conventional redox active materials such as polyvinylferrocene, viologen-based polymers, viologen/quinone polymers, polycations charge compensated with electroactive anionic metal complexes, and Prussian blue demonstrates the characteristics of microelectrochemical transistors based on redox materials for which the region of $V_G$ where $I_D>0$ is very narrow ($\approx 200$ mV) and is dependent on the chemical environment. Generally, any reversibly redox active molecule can be incorporated into a polymer of some sort, allowing preparation of a microelectrochemical transistor that shows a peak in $I_D$ at $V_G=E^{\circ'}$. For $V_G>100$ mV away from $E^{\circ'}$, $I_D$ approaches zero, because the self-exchange mechanism for charge transport requires a significant concentration of reduced and oxidized centers. Since $I_{D(max)}$ occurs at $E^{\circ'}$, the value of $I_D$ at fixed $V_S$ and $V_D$ will depend on the chemical environment whenever the redox material has a chemically dependent $E^{\circ'}$.

Redox reagents are known that respond to gases ($O_2$, $H_2$, CO, etc.) and ions ($H^+$, $Li^+$, $Na^+$, etc.). A principal drawback with conventional redox polymers is the low conductivity compared to that of conducting polymers. The tradeoff is a remarkable range of intrinsic chemical specificity.

Many metal oxides undergo reversible electrochemical reactions that, like redox reactions of molecular polymers, are accompanied by changes in conductivity. The electroactive oxides exhibit electrochemical behavior that depends on the environment to which the oxide is exposed. For example, $WO_3$, $Ni(OH)_2$, and $RuO_2$ all show pH-dependent properties that stem from the involvement of H. in the reversible reduction of the oxide.

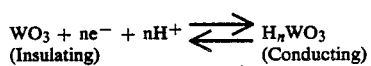

$$WO_3 + ne^- + nH^+ \rightleftarrows H_nWO_3 \quad (2)$$
(Insulating) (Conducting)

The potential at which the oxide becomes conducting depends on pH such that a microelectrochemical transistor shows a pH dependent $I_D$–$V_G$ characteristic. This intrinsic chemical dependence of the electrochemical behavior of the oxides allows their use as the active material in chemically sensitive transistor devices.

$WO_3$ has received considerable attention in recent years as an electrochromic material which becomes colored upon reduction, as described by Dautremont-Smith et al. in *Ind. J. of Pure and Appl. Phys.* 24, 19 (1986). The reduced, cation-intercalated species, $M_nWO_3$, where $M=H^+$, $Na^+$, or $Li^+$, has also been reported to be conducting. In addition, there have been reports on anodically grown, polycrystalline, colloidal, and dispersed n-type semiconducting $WO_3$ (DiQuarto et al., *Sol. Energy Mat.* 11,419 (1985) and Electrochim. Acta 26, 1177 (1981); Desilvestro et al., J. Phys. Chem. 89, 3684 (1985); Nenadovic et al., *J. Phys. Chem.* 88, 5827 (1984); W. Erbs *J. Phys. Chem.* 88,4001 (1984).

The oxidation of $Ni(OH)_2$ has been of great interest to electrochemists since the turn of the century when Edison patented the use of $Ni(OH)_2$ as the anode in alkaline electrochemical storage cells. A tremendous amount of research since then has been devoted to understanding this complex reaction. There are several methods of preparing electroactive $Ni(OH)_2$ films, including direct growth of Ni metal electrodes and electrodeposition onto conducting substrates by a variety of cathodic and anodic techniques. In addition to being an important material for use as a battery electrode, $Ni(OH)_2$ is also an electrochromic material, becoming colored upon electrochemical oxidation.

Figure 4:
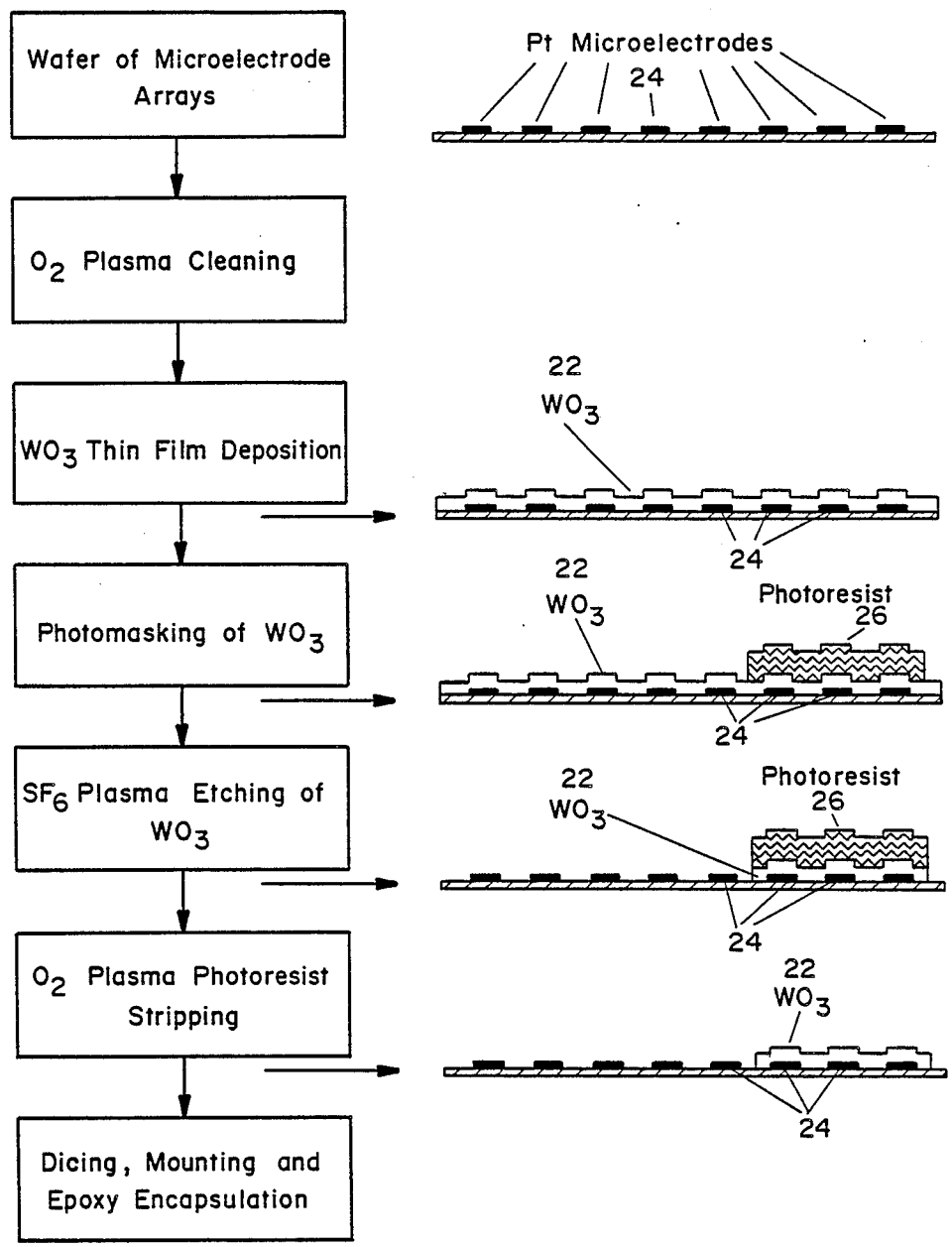
FIG. 4 is a flow chart for fabrication of $WO_3$-based devices according to the present invention.

Although transition metal oxides have interesting properties, they are generally not considered to be conductors and therefore to have utility in the transfer of signals proportional to a chemical or electrical input. They are also different from the electrochemically polymerizable redox materials such as polypyrrole not only because of their substantially lower conductivity but because they can be insulating when oxidized and conducting when reduced. However, metal oxides have an important advantage connected with the fabrication of devices. Many metal oxides can be deposited and patterned using more or less conventional microfabrication techniques. For example. FIG. 4 illustrates a process for the fabrication of a $WO_3$ based device 20 where $WO_2$ 22 is deposited by a plasma deposition onto $O_2$ plasma cleaned Pt microelectrodes 24 and then selectively removed with an $SF_6$ plasma after first protecting the $WO_3$ to be retained with photoresist 26. The protecting photoresist is subsequently removed from the $WO_2$ by stripping with an $O_2$ plasma. The process is completed by mounting and encapsulating the device.

Further, oxide-based microelectrochemical transistors have two significant advantages over previously developed chemical sensors. The first is that the physical volume of the sensing element is smaller than for other sensors, in principle requiring an exposed surface area of approximately 50 microns x approximately 7 microns, and a depth of approximately 0.1 microns at separations in the range of two microns. The required surface area can be decreased significantly by decreasing the spacing between electrodes. The second advantage of these sensors is that they are able to amplify a chemical signal. A conventional electrochemical detector gives a current response equal to the amount of material oxidized or reduced; in contrast, the output of a microelectrochemical transistor is the drain current and can exceed the current needed to oxidize or reduce the gate region by at least a factor of 1000. By changing the geometry of the microelectrodes, much larger amplifications can be observed.

Microelectrochemical devices based on the electroactive metal oxides show persistent, reproducible response to pH variation for fixed $V_G$ and $V_D$ for periods of time exceeding one hour. The response time of the oxide-based devices is like that of conventional redox polymers, slow compared to the response time of conducting polymers such as polyaniline. However, the response time of less than one second to pH changes is adequate for many sensor applications.

The microelectrochemical transistors based on conducting polymers, conventional redox polymers, and electroactive oxides can all be operated in fluid solutions containing electrolytes. By modifying a microelectrode array with a spot of Ag epoxy as a reference electrode, redox active material for the transistor, and an ionic conducting polymer as the electrolyte solution, all of the components for a microelectrochemical transistor can be confined to the chip, as shown in FIG. 1. The characteristic response of a WO$_3$-based transistor with poly(vinyl alcohol)/H$_3$PO$_4$ as the electrolyte system is similar to that in aqueous acid.

Polyaniline, poly(3-methylthiophene), or other redox active polymer, can be electrochemically deposited onto any of the other microelectrodes to provide a device with additional functions. As with the polymer device shown in FIG. 1, the resulting two transistor chip is completed by depositing a spot of Ag epoxy as a quasi-reference, coating with poly(vinyl alcohol)/H$_3$PO$_4$, and using a clean microelectrode within the array as the counterelectrode. The two transistors can be operated independently, each showing the response expected of an isolated device.

The conducting polymer/WO$_3$ chip is particularly interesting since the WO$_3$-based device turns on upon reduction while the conducting polymer device turns on upon oxidation. Thus, application of a potential (negative lead to WO$_3$, positive lead to conducting polymer) across the sources of the two devices will turn them both on. Such a device is therefore a "self referencing" microelectrochemical transistor where the magnitude of $V_G$ required for turn on of the two transistors depends on the properties of the redox active materials.

In contrast to the devices made with materials such as those in the parent application, U.S. Pat. No. 4,721,601, the devices of the present invention are based on metal ion based inorganic redox materials, materials not generally considered to be conducting, i.e., whose minimum resistance is in the range of $10^2$ to $10^4$ ohms. Only by using microfabrication techniques and small interelectrode separations can these devices be made to function as sensors and transistors. For example, for a typical Ni(OH)$_2$-based device consisting of a 0.5 to 1.0 micron thick cathodically deposited Ni(OH)$_2$, film overlaid on 50 micron long gold microelectrodes separated by a distance of 1.2 microns, the resistivity of the Ni(OH)$_2$ is 20 to 40 ohm-cm. This value is five or six orders of magnitude higher than for elemental metals, and about equal to the resistivity of highly doped single crystal semi-conductors.

However, while the resistivity is high for a "conducting" material, the potential dependence of the resistivity leads to novel applications, especially as pH sensors and as chemical sensors having transistor-like properties. Further, although the power amplification and response times of the transition metal oxide devices are not comparable to those of conducting materials such as poly(3-methylthiophene) and polyaniline that can amplify power at frequencies of 1 KHz, they can function at very high pH, a regime where none of the other conducting materials characterized to date are durable.

The pH-sensitive redox processes leading to changes in conductivity of oxide-coated microelectrodes are demonstrated using pH-sensitive WO$_3$ or Ni(OH)$_2$-based microelectrochemical transistors. The dependence of the electrochemical processes which alter the conductivity of WO$_3$ and Ni(OH)$_2$ is common to all of the oxides mentioned above, and thus all the microelectrode-derivatized oxides function as pH-sensitive microelectrochemical transistors, each displaying a unique pH sensitivity.

The ability to accurately control the placement of transition metal oxides on arrays of closely spaced microelectrodes provides a means for the preparation of pH sensitive microelectrochemical devices.

Several variations of the pH sensors are possible, as described above. In another embodiment, a pH-sensitive p-n-p transistor can be prepared by derivatizing adjacent microelectrodes with poly(3-methylthiophene), WO$_3$, and poly(3-methylthiophene).

The devices of the present invention can also be used to sense any chemical which is thermodynamically and kinetically capable of turning an oxide-based device either on or off, through chemical oxidation or reduction, directly or by mediation. For example, glucose can be sensed by a surface modified WO$_3$-based microelectrochemical transistor. The surface of the WO$_3$ is derivatized with glucose oxidase, using any of a number of methods known to those skilled in the art, to produce a system where reduction of WO$_3$ by glucose is effected through the glucose oxidase. The concentration of glucose is ascertained by measurement of the current passing between adjacent biased WO$_3$-connected microelectrodes since the conductivity of the WO$_3$ is dependent on the chemical reduction of WO$_3$ by the glucose. A second way to assess the glucose concentration involves taking the derivative of the measured current to the rate of WO$_3$ reduction, then relating the rate to the glucose concentration using Michaelis-Menton kinetics.

All the oxide- and mixed oxide-based devices act as sensors of molecules which can turn on, i.e., render more conducting, the oxides which comprise part or all of the devices. WO$_3$-based devices, by themselves or in conjunction with derivatized enzymes or other mediators, are sensors of the reduced form of all molecules possessing a redox potential, E$^{o\prime}$, of $-0.2$ V vs. SCE or less, at pH 7. The specificity and rate of sensing depend on the kinetics of electron transfer from the molecule to be sensed to the device.

The present invention is further described by the following non-limiting examples of the construction and application of transition metal-oxide based microelectrochemical devices.

Preparation, Masking, Cleaning, and Encapsulation of Microelectrode Arrays:

Microelectrode arrays were constructed as generally described in U.S. Pat. No. 4,721,601 and continuation-in-part U.S. Pat. No. 4,717,673 issued Jan. 5, 1988 to Wrighton et al. entitled "Microelectrochemical Devices" using photolithographic techniques to form arrays of microelectrodes of inert, highly conductive metals, preferably gold or platinum, (50 microns long, 2.4 microns wide, and 0.1 microns thick, separated by 1.2 microns) on an insulating substrate, preferably SiO$_2$, or Si$_3$N$_4$. Glassy carbon and SnO$_2$ electrodes can also be used. SnO$_2$ electrodes are useful for transmission studies.

The microelectrode array was then packaged. In some cases an additional layer of Si$_3$N$_4$ was deposited to insulate the entire device except for the actual wire array and the contact pads. When Si$_3$N$_4$ was not used, the devices were insulated using epoxy. The packaged assemblies were then cleaned immediately before deposition with an O$_2$ plasma etch (150W) for between 5 and 10 minutes to remove any residual photoresist or epoxy from the microelectrodes. F-doped SnO$_2$ electrodes were cleaned electrochemically prior to Ni(OH)$_2$ deposition by passing anodic, cathodic, and then anodic current at 1 mA/cm$^2$ for 30 seconds each in 5 M KOH, and In-doped SnO$_2$ was cleaned by successive sonication in H$_2$O, isopropanol, and hexane.

The microelectrodes for Ni(OH), deposition were then cycled individually at 200 mV/s four or five times from −1.6 to −2.1 V vs. SCE in a 0.05 M pH 7 phosphate buffer. Hydrogen evolution at the negative potential limit further cleans the microelectrodes and ensures reproducible electrochemical behavior. The microelectrodes were then tested by examining their behavior in a 0.2 M LiCl solution containing 5 mM $Ru(NH_3)_6^{3+}$. A well-defined current-voltage curve at 50 mV/s for the reduction of $Ru(NH_3)_6^{3+}$ is characteristic of a "good" microelectrode.

The chips are masked prior to $WO_3$ or $Ni(OH)_2$ deposition to ensure deposition in the desired locations, either by manually applied aluminum foil masks or by photolithographically prepared $Si_3N_4$ masks 0.1 micron thick. After deposition of $WO_3$ or $Ni(OH)_2$, electrical contact to individual wires is made and the devices encapsulated.

$WO_3$ is deposited using a modification of the method of Miyake et al *J.Appl.Phys.* 54, 5256 (1983). Polycrystalline $WO_3$ is sputtered downhill from a sintered polycrystalline $WO_3$ target onto half-masked macroscopic Au, Pt, and $SnO_2$ electrodes, and onto masked microelectrodes using an R. D. Matthis SP 310 RF diode sputtering system. The power is provided by an RF Plasma Products power supply. The diameter of the cathode is 3.5 inches. The samples are initially presputtered for 15 minutes for further cleaning. Deposition then takes place onto samples heated to 676° K. for 8 to 12 minutes, depending on the thickness of $WO_3$ desired. The sputtering gas is a 10% $O_2$/Ar mixture for both the presputtering and the actual deposition. These conditions allow simultaneous preparation of many samples having a 0.1–0.2 micron thick adherent film of $WO_3$. The sample thickness is determined by measuring step profiles on derivatized $WO_3$ microelectrodes using either a Tencor Instruments Alpha-Step 100 or a Sloan Dektak surface profiling system.

For deposition of $Ni(OH)_2$ onto $SnO_2$ electrodes, the electrodes are immersed in 0.01 M $Ni(NO_3)_2$ and cathodic galvanostatic deposition performed at 0.04 $mA/cm^2$ for 8 minutes to produce 0.1 micron thick adherent films of $Ni(OH)_2$. The potential of the working electrode during the deposition is approximately −0.7 to −0.8 V vs. SCE.

The current densities used for galvanostatic deposition of $Ni(OH)_2$ on $SnO_2$ are too low to control with accuracy on gold or platinum microelectrode arrays so deposition onto the microelectrodes is performed using potentiostatic control. The same method can be used for deposition onto $S_nO_2$ electrodes. Adherent films are obtained by holding the potential of the microelectrodes between −0.75 and −0.80 V vs. SCE for 60–100 seconds in aqueous solutions containing either 0.01 M $Ni(NO_3)_2$, 0.1 M $NI(NO_3)_2$, 0.1 M $Ni(NO_3)_2$/0.1 M $KNO_3$, or 0.05 M $Ni(NO_3)_2$/ 0.05 M $Na(NO_3)$. After an initial spike, the cathodic current decreases during the deposition, indicative of formation of an insulating film of $Ni(OH)_2$ on the microelectrodes. $Ni(OH)_2$ can be deposited selectively onto individual microelectrodes by holding the adjacent electrodes onto which $Ni(OH)_2$ is not to be deposited between 0.2 V and 0.3 V vs. SCE. The derivatized microelectrodes are rinsed in triply distilled $H_2O$ or pH 12 $CO_3^{2-}$ /$CO_3H$- buffer, and characterized electrochemically in 1 M KOH.

when there is no decrease in the current during the deposition, the electrochemistry of the resulting films is "poor" in that well formed cyclic voltammograms for the $Ni(OH)_2 \rightarrow NiO(OH)$ interconversion cannot be detected. It has been observed that properties of Ni(OH)₂ electrodes are critically dependent upon deposition conditions. The conditions used here for microelectrodes typically produce films of $Ni(OH)_2$ approximately 0.5–1.0 micron thick. Sharp single peaks are observed for both oxidation and reduction of $Ni(OH)_2$ films when $KNO_3$ or $NaNO_3$ is added to the electrolyte.

$RuO_x$ deposition is carried out in a freshly prepared 5 mM $K_2RuO_4$/1 M NaOH solution by cycling a macroscopic working electrode at 100 mV/S between −0.2 and −0.8 V, leading to growth of a wave centered at −0.54 V.

Macroscopic electrodes for characterization and comparison with films on the microelectrode arrays are prepared using similar techniques.

In situ transmittance measurement are obtained with a Bausch and Lomb Spectronic 2000 spectrophotometer. The spectroelectrochemical cell was fashioned from a standard polystyrene cuvette with a 1 cm path length. Time-dependent transmittance at 500 nm was measured using a single beam spectrophotometer with components from photon Technology International, Inc. and included a Model HH150 high efficiency arc lamp source with a 150 W xenon lamp (Osram) and water filter, monochromator, sample compartment and photomultiplier unit with a IP28 photomultiplier tube (RCA). Switching measurements were recorded on a Bausch Mark 200 strip chart recorder. Time-dependent optical absorbance at 500 nm was measured using a Hewlett-Packard 8451A rapid scan spectrometer.

Electrochemical experiments were performed using Pine Instruments RDE-4 Bipotentiostats and Kipp and Zonen X-Y-Y'-T or X-Y recorders for microelectrode studies and a PAR 173/175 or Model 273 potentiostat/programmer in conjunction with a Houston 2000 X-Y recorder for SnO, studies and with macroscopic electrodes. The Kipp and Zonen recorders or Tektronix storage oscilloscopes with camera attachments were used for time based studies. A sinusoidal waveform was obtained using the internal oscillator output of a PAR 5204 lock-in amplifier. UV-visible spectra were recorded using either a Hewlett-Packard Model 8451-A diode array spectrophotometer or a Cary 17 spectrophotometer. Optical micrographs of microelectrodes were obtained with a Polaroid camera mounted on a Bausch and Lomb Model optical microscope. Reproducible chemical signals were delivered to microelectrodes using Hewlett-Packard Model 1084B high pressure liquid chromatograph pumps.

Characterization of RF Sputtered $WO_3$ Films

RF sputtered films of $WO_3$ on macroscopic electrodes were characterized by examining the electrochemistry of thin films of polycrystalline $WO_3$ on optically transparent $SnO_2$ electrodes at pH 4.5. Intense coloration in the visible region accompanies electrochemical reduction. The significant changes in the absorbance at 700 nm occur from −0.3 to −0.8 V vs. SCE, where reduction is observed by cyclic voltammetry. No significant spectral changes occur beyond −1.0 V vs. SCE for $WO_3$ at pH 4.5. The electrochemical potential of the cyclic voltammetric wave (and of coloration) moves with pH. At pH 0, lower reducing potentials are needed to reduce the $WO_3$. Basic solutions necessitate more reducing potentials to reduce the $WO_3$.

Potential step measurements confirm that charge can be reversibly added to and withdrawn from $WO_3$. At pH 4.5, integrated currents from potential steps from +0.6 V to more reducing potentials indicate that at potentials negative of −0.4 V vs. SCE, "metallic" behavior is obtained, as judged by linearity of charge vs. potential plots on macroscopic $SnO_2$ and gold electrodes. The data indicate that $WO_3$ has a capacity of approximately 100 F/cm$^3$, somewhat smaller than that for poly(3-methylthiophene).

The cyclic voltammetry of arrays of microelectrodes coated with a 0.15 micron layer of $WO_3$ is invariant with time in acidic, neutral, and basic solutions. The results indicate that the shape of the voltammogram depends, among other factors, on $k_f$, the charge transfer rate constant, and on the hydrogen atom diffusion coefficient within the film, $D_H$. The data is consistent with a material having a small $D_H$ (approximately $1 \times 10^{-9}$ cm$^2$/sec) and $k_f$, (approximately $10^{-2}$ sec$^{-1}$ (mole/cm$^3$)$^{-2}$. The consequences of small values for $D_H$ and $k_f$ are a slow response time, manifested as a delay in oxidation of reduced $WO_3$ upon scan reversal. Anodically grown $WO_3$, which has a rapid response time, has larger values for both $D_H$ (approximately $5 \times 10^{-8}$ cm$^2$/sec) and $k_f$ (approximately 7.2 sec$^{-1}$(mole/cm$^3$)$^{-2}$).

Integration of the voltammograms indicates roughly $6 \times 10^{-8}$ C is associated with the electrochemical process upon scanning from +0.2 to −0.4 V vs. SCE. Assuming that the density of $WO_3$ on the microelectrodes is that of the pure material, and that the surface area of $WO_3$ on the microelectrode array is $7 \times 10^{-9}$ m$^2$, five times the area bounded by the wires themselves, and further assuming a one electron reduction per $WO_3$ unit, one can calculate that, as a lower limit, approximately 2.5% of the total quantity of $WO_3$ in electrical contact with the wires is reversibly reduced and reoxidized in a single scan from 0.2 to −0.4 V vs. SCE.

The resistance of $WO_3$ connecting two or more microelectrodes can be measured by bringing both electrodes to a given $V_G$, and then scanning the potential of one microelectrode at a small voltage, approximately ±25 mV about $V_G$. The drain voltage, $V_D$, is the potential difference between the two electrodes developed by scanning one microelectrode.

Unlike the conducting organic polymers polyaniline and poly(3-methylthiophene), $WO_3$ does not exhibit very high resistance in the insulating state. The resistance changes by over three orders of magnitude from 0.0 to −0.9 V vs. SCE at pH 6.6. The resistance may reach limits of just over $10^2$ and $10^7$ ohms, but the resistance of the material never changes by more than four orders of magnitude in aqueous solution. For example, for particular samples, the resistivity of as deposited $WO_3$ is extremely dependent on deposition conditions, varying from $10^3$ ohm-cm to $10^9$ ohm-cm. Since polycrystalline $WO_3$ is a n-type semiconductor, the conductivity of the material is expected to be reasonably high in electrolyte-containing solutions, where the concentration of potentially doping impurities is high.

The ruggedness of the oxide, relative to conducting organic polymers, is evidenced by the stability of the material in the fully reduced (conducting) state. Excursions to −1.5 V vs. SCE, 10 250 mV negative of the $V_G$ of maximum conductivity (at p7), do not cause any irreversible damage to the oxide, in contrast to poly(3-methylthiophene).

Another way to quantitatively assess the effect of $V_G$ on the conductivity of a $WO_3$ film is to measure $I_D$ as a function of $V_G$, at a fixed $V_D$. The $I_D$–$V_G$ characteristic result from properties intrinsic to $WO_3$. The values of $V_G$ which give significant $I_D$, the maximum slope of the curve (the transconductance), and the maximum value of $I_D$ for a given $V_D$ will differ from material to material. As expected, the $I_D$–$V_G$ curves for $WO_3$ depend on the pH. The maximum drain current obtained for a 200 mV drain voltage is 550 microamps, which exceeds that achieved with polypyrrole or polyaniline, but is less than the 1 mA found for poly(3-methylthiophene)-based devices of the same geometry. The reduced state of $WO_3$ is several orders of magnitude more conductive than the conducting (oxidized) state of $Ni(OH)_2$, indicating that a large variation in $I_D$–$V_G$ characteristics may be found among metal oxide-based microelectrochemical devices. It is important to note that the maximum drain current of 550 microamps is achievable at approximately pH 7 by moving $V_G$ to a strongly reducing potential so that, at approximately pH 7, the entire $I_D$ range of the device is accessible. Under basic conditions, an $I_D$ of 550 microamps cannot be obtained at any $V_G$. The maximum slope of the $I_D$ vs. Vs plot, transconductance, at pH 0, is around 12 mS/mm of gate width, an order of magnitude less than that obtained for poly(3-methylthiophene). At pH 6.6, the transconductance is approximately 10 mS/mm of gate width. *pH Dependency of WO$_3$-based devices.*

The $WO_3$ device can be used as a pH sensor since a steady state measurement at fixed $V_G$ and $V_D$ gives an $I_D$ which is solely a function of pH, since other cations in solution which are capable of intercalation into $WO_3$, Li$^+$, Na$^+$ and K$^+$, do not interfere with the pH response. By way of example, a $WO_3$-based microelectrochemical transistor was placed in 0.05 M, pH 5 acetate buffer with $V_G$=0.0 V vs. SCE and $V_D$=150 mV. A stable $I_D$ of 265 nA was produced. Li$^+$ was added in the form of $Li_2SO_4$ to a concentration of 0.32 M. The $I_D$ moved to 280 nA, a change of only 6% for a four order of magnitude excess of interfering ion. In another study, the effect of interfering ions on $I_D$–$V_D$ plots for various $V_G$'s was determined. Saturated KCl and NaCl solutions and 2 M LiCl, all at pH 7, gave $I_D$–$V_D$ plots identical to those obtained in 0.1 M $Na_2SO_4$ pH 7. Also addition of base to I7 a 2 M LiCl pH 5.0 solution moved the $V_G$ for turn on to more reducing potentials.

Figures 5A, 5B:
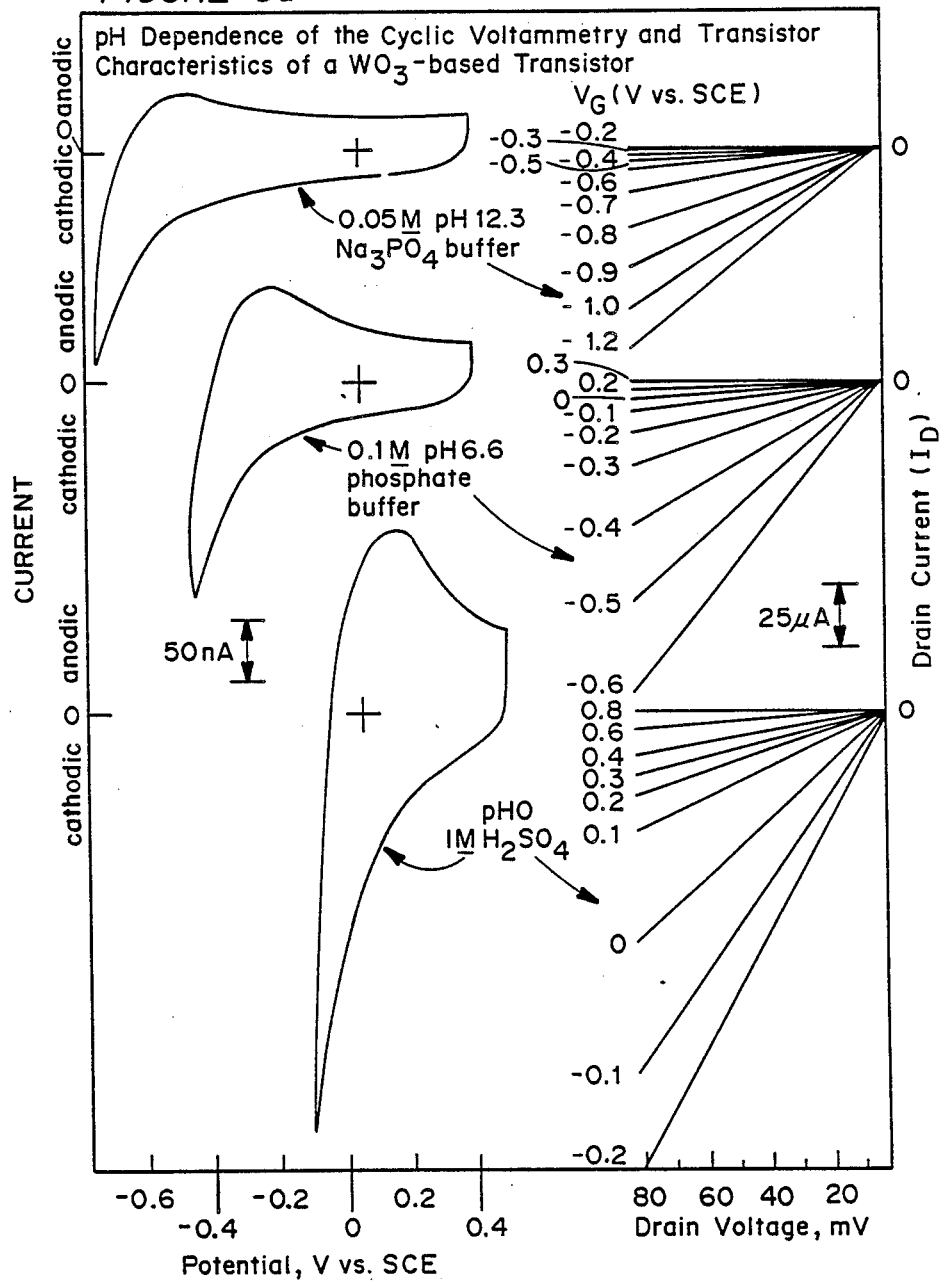
FIG. 5a to 5b the cyclic voltammetry (a) and $I_D$ vs. $V_D$ (at fixed $V_G$) transistor characteristics of $WO_3$-connected microelectrodes at three different pH's, recorded at 200 mV/s with $V_D$ varied at 10 mS/s.

The dependence on pH of the reduction of $WO_3$ causes the transistor properties of $WO_3$-connected microelectrodes to vary 21 with pH. Cyclic voltammetry of $WO_3$-connected microelectrodes at acidic, neutral, and basic values of pH, shown in FIG. 5, demonstrates that reduction occurs at more negative potentials at basic pH and at more positive potentials at acidic pH. In addition, there is a slight decrease in the amount of charge injected at basic pH, as reflected by integration of the voltammograms. When the pH is lowered, the cyclic voltammogram is identical to that obtained initially in acidic solution There may be a reversible pH-induced structural change which blocks a percentage of $WO_3$ sites to reduction. FIG. 5b shows, at the same three pH's, linear plots of $I_D$ vs. $V_D$ (at fixed $V_G$) for several $V_G$'s, also demonstrating a pH dependence. Thus, at $V_G$= −0.2 v vs. SCE, the device is completely turned off at pH 12.3, slightly on at pH 6.6, and nearly fully turned on at pH 0. At a given pH, the slope of the $I_D$–$V_D$ plots increases as $V_G$ is moved negatively, again illustrating that the resistance between $WO_3$-connected microelectrodes decreases as $WO_3$ is reduced.

Figure 6:
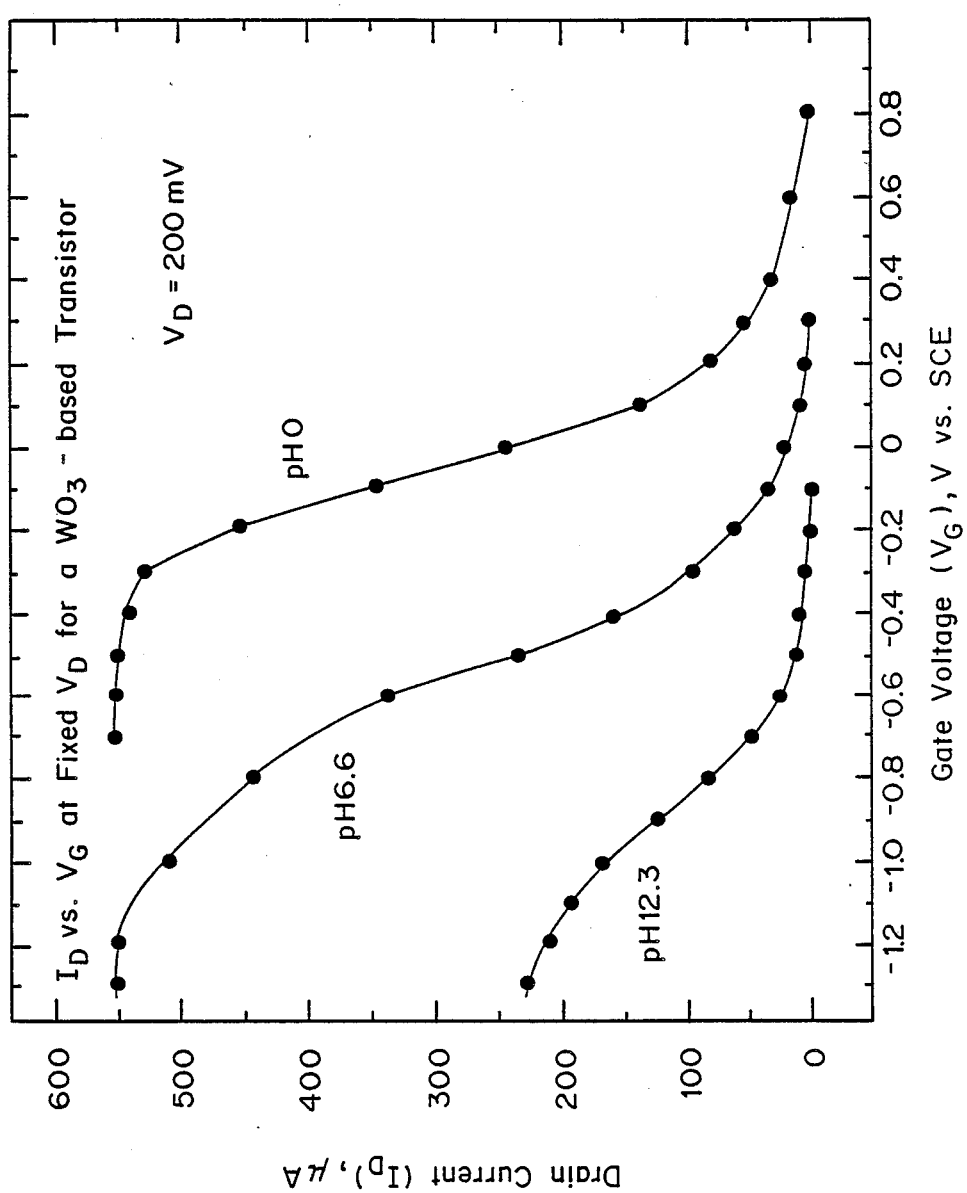
FIG. 6 is a plot of $I_D$ vs. $V_G$ at fixed $V_D$ (200 mV) at pH 0, pH 6.6, and pH 12.3 for $WO_3$ coated microelectrodes.

The $WO_3$ device functions as a good pH sensor since variation in $I_D$ is observed upon variation of pH in a solution in contact with a $WO_3$-based transistor at fixed $V_G$ and $V_D$ and the device is durable in aqueous solutions (stable from pH 0–13). Further, there is the lack of interference from cations. This is further demonstrated using the two solvent reservoirs and pumps of a HPLC to create a flowing aqueous stream whose pH can be changed in order to deliver a reproducible pH change to the microelectrode. Using 0.1 M pH 7.2 phosphate buffer in one reservoir and 0.1 M pH 3.9 acetate buffer in the other, the pH of the solution flowing past the $WO_3$-coated microelectrode can be cycled. The results of this study are shown in FIG. 6, where $V_G = -0.5$ V vs. SCE, $V_D = 150$ mV, and the solvent flow rate is 6.0 ml/min. $I_D$ is monitored over time and is found to be 0.08 microamps for the pH 7.2 solution and 0.08 microamps for the pH 3.9 solution. The changeover from one pH to the other requires approximately 45 seconds; $I_D$ reaches the steady state value within 90 seconds of when the transistor is exposed to the new pH solution. The stream was continuously flowed past the microelectrode for 6 h without any degradation in the response time or the steady state $I_D$ at either pH.

All the characteristics usually associated with conventional transistors, changes in the slopes of $I_D$ vs. $V_D$ plots as $V_G$ is varied (FIG. 5), sigmoidal plots of $I_D$ vs. $V_G$ at fixed $V_D$, and power amplification with well-behaved and separately measurable $I_G$ and $I_D$ (FIG. 6), have been demonstrated.

Figure 7:
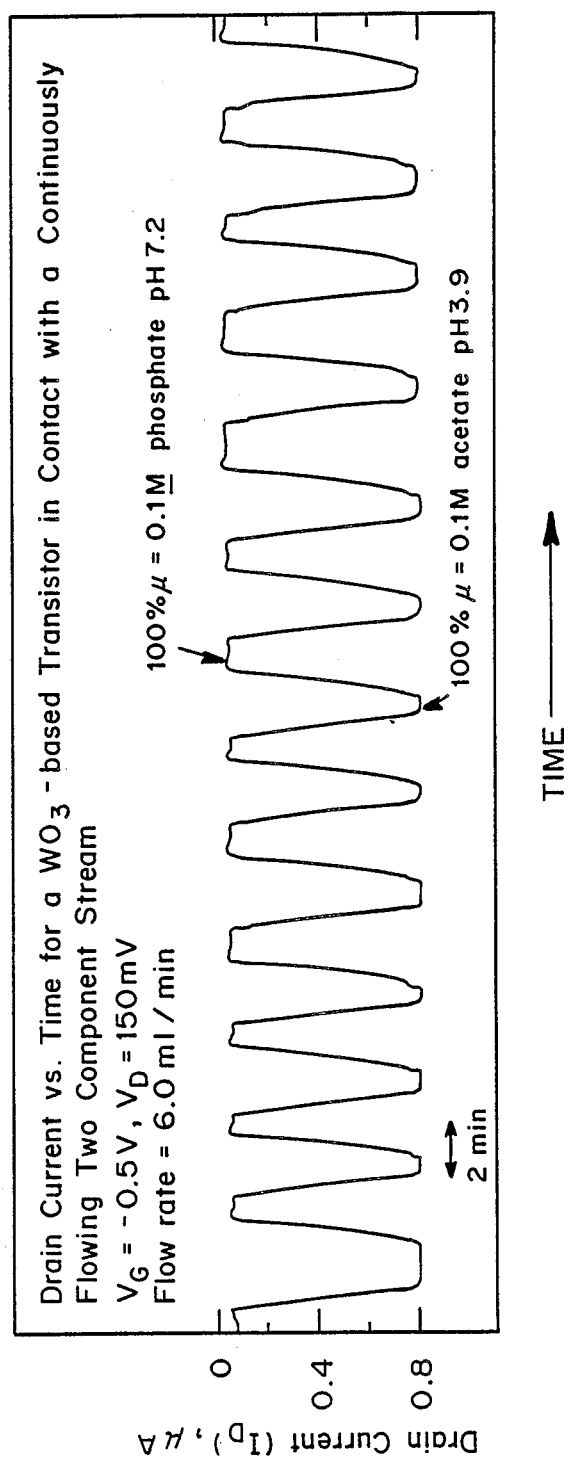
FIG. 7 is a plot of $I_D$ vs. time for a $WO_3$-based transistor upon variation of pH in a continuously flowing stream, where $V_G = -0.5V$ vs. SCE and $V_D = 150$ mV.

The effect of pH on the real-time $I_D$ response, at fixed $V_G$ and $V_D$, of $WO_3$-connected microelectrodes exposed to pH change in a flowing stream demonstrates the pH dependence of the electrochemical reduction of $WO_3$. 0.1 M pH 7.2 phosphate buffer was placed in one reservoir and 0.1 M pH 3.9 acetate buffer was placed in the other. The results are shown in FIG. 7, where $V_G = 0.5$ V vs. SCE, $V_D$-150 mV, and solvent flow rate is 6.0 ml/min. $I_D$ is monitored over time and found to be 0.08 microamps for the pH 7.2 solution and 0.8 microamps for the pH 3.9 solution. The changeover from one pH to the other requires approximately 45 seconds; $I_D$ reaches steady state within 90 seconds of when the transistor is exposed to the new pH. The stream was continuously flowed past the microelectrode for six hours without any degradation in the response time on the steady state 1a at either pH.

The full range of $I_D$ is achievable at pH=7 through control of $V_G$. The transconductance of these microelectrochemical transistors is sufficiently large to insure significant $I_{in\ the\ VG}$ range $-0.25$ to $-0.8$ V vs. SCE at pH 7, where the redox potential of many biological reducing agents are found, so that the $WO_3$-based devices may be of value in sensing biological molecules.

Characterization of $Ni(OH)_2$ films

F-doped $SnO_2$ and In-doped $SnO_2$ (ITO), are used for optical measurements of $Ni(OH)_2$ based devices. The optical transmittance of F-doped $SnO_2$ is about 80% in the visible region.

Figure 8:
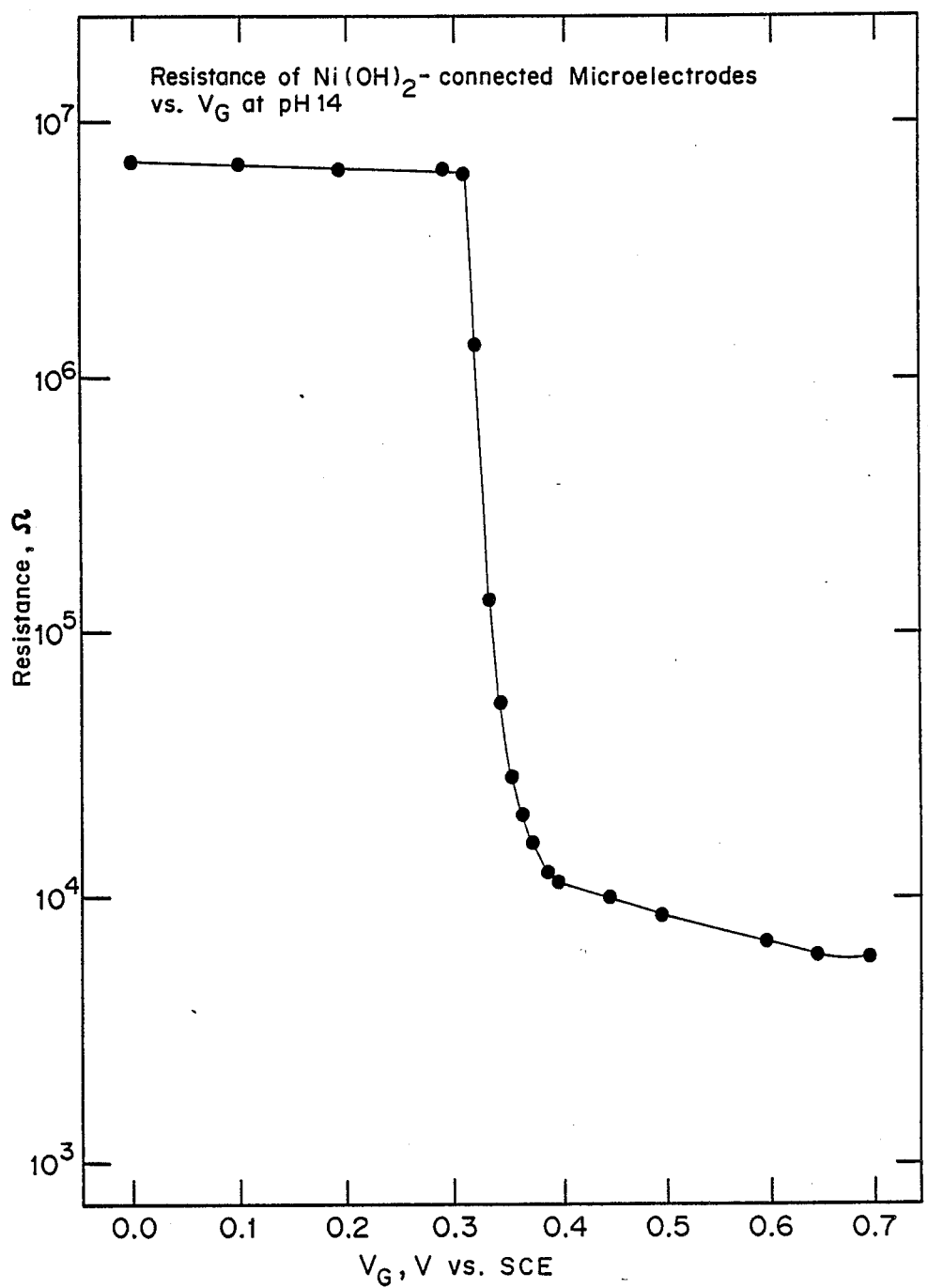
FIG. 8 is a plot of the resistance of $Ni(OH)_2$-connected microelectrodes as a function of $V_G$ at pH 14, where one microelectrode is scanned at ±5 vM about $V_G$ at 2 mV/sec and $V_G$ is moved anodically.

An important property of microelectrode-based transistors is the resistance, as a function of $V_G$, between two microelectrodes connected by a redox active material. In FIG. 8, the resistance as a function of $V_G$ is illustrated for $Ni(OH)_2$-connected microelectrodes at pH 14. As with $WO_3$, the change in resistance of $Ni(OH)_2$ is associated with injection or withdrawal of charge in an electrochemical redox process. Changes in resistance are observed by varying $V_G$ through the region where redox processes occur. The current passing between electrodes is measured and related to the resistance by Ohm's law. Since the oxidation wave for $Ni(OH)_2$ is particularly sharp, it is important that the potential difference ($V_D$) developed by scanning one microelectrode is small enough not to seriously affect the ratio of oxidized to reduced material. Thus, typical $V_D$ excursions are $\pm 3$–5 mV. 35 The resistance of $Ni(OH)_2$-connected microelectrodes varies by three orders of magnitude, from approximately $10^7$ ohms to approximately $10^4$ ohms, as $V_G$ is varied from 0.0 up to 0.7 V vs. SCE. The resistance of $Ni(OH)_2$-connected microelectrodes in the oxidized, conducting state is much higher than for reduced $WO_3$ or oxidized conducting organic polymers derivatized on microelectrodes. In the insulating state, the resistance, as for $WO_3$, is lower than for the conducting organic polymers. The resistance of the oxide in the "insulating" state may be increased by decreasing the concentration of doping impurities in solution.

A manifestation of the sharpness of the oxidation wave for $Ni(OH)_2$, compared to other redox active conducting materials, is the slope of the resistance-$V_G$ plot, shown in FIG. 8. Nearly the entire three orders of magnitude change in resistance occurs between $V_G = 0.3$ and 0.4 V vs. SCE, the sharpest change in resistance found to date for any conducting material derivatized onto microelectrodes. Calculations reveal that, in the conducting state, the resistivity of cathodically deposited $Ni(OH)_2$ is 20–40 ohm-cm, five or six orders of magnitude higher than for elemental metals, and about equal to the resistivity of highly doped single crystal semiconductors.

Evidence that $Ni(OH)_2$-based microelectrochemical transistors function as electrical power amplifiers is illustrated by comparing the magnitudes and relationships of $V_G$, $I_G$, and $I_D$, for a slow triangular potential variation between 0 V and 0.45 V vs. SCE. Three adjacent, $Ni(OH)_2$-connected microelectrodes were used in these studies. $I_G$ was recorded for the center microelectrode, while $I_D$ was recorded for a separate circuit between the outer "source" and "drain" microelectrodes.

$I_G$ and $I_D$ almost equal zero at $V_G = 0$ vs. SCE where $Ni(OH)_2$ is reduced and insulating. As $V_G$ is scanned positive, anodic $I_G$ is observed until all the material in the gate region has been oxidized. When $V_G$ reaches its upper limit, $I_G$ should once again be zero. Upon scan reversal, the reverse electrochemical process is a reduction. $I_D$ should equal zero until enough charge is withdrawn from $Ni(OH)_2$ in the gate circuit to turn on the device, and should return to zero when sufficient charge is injected to turn off the device. A $Ni(OH)_2$ device constructed as described nearly obeys the relationships above. The integrated $I_G$ is greater for oxidation than for reduction, due to the oxidation of excess $OH^-$ in the lattice, and this may contribute to the non-ideal relationship between $I_G$ and $V_G$. $I_D$ behaves as expected at $3.8 \times 10^{-2}$ $H_2$. It is important to note, however, that $I_G$ does not go to zero if $V_G$ is held at the positive limit because $OH^-$ is oxidized.

Using the cathodic portion of the cyclic voltammogram as an indication of $I_G$, the maximum amplification observed for $Ni(OH)_2$ devices is approximately 20. The slow operating speed of $Ni(OH)_2$-based microelectrochemical transistors is limited by the slow electrochemistry of the $Ni(OH)_2$ films. $Ni(OH)_2$-based transistors do not amplify power at frequencies higher than approximately 1 mHz.

The temperature dependence of $I_D$ of $Ni(OH)_2$-based transistors was also measured. The Arrhenius form of the temperature dependence of $I_D$ is shown by $I_D=I_D° \exp[-E_a/RT]$, where $I_D°$ represents a collection of constants, R is the gas constant, T is the temperature in degrees Kelvin, and $E_a$ is the activation energy for conductivity. $E_a$ should not depend on $V_G$, since [NiO(OH)]/[Ni(OH)$_2$] is fixed at a given $V_G$. A reasonably large temperature dependence is found; the energy of activation for charge transport is calculated from the slope of the best-fit line and found to be 27±2 kJ/mol, at $V_G$=0.35 V vs. SCE. The temperature dependence of the redox potential was found to be negligible by cyclic voltammetery in the temperature range investigated. Furthermore, determination of $E_a$ for a different sample at $V_G$=0.45 V vs. SCE and $V_D$=50 mV, where Ni(OH)$_2$ is completely oxidized, gave a value of 23±2 kJ/mol. Thus, it appears that the temperature dependence of $I_D$ is related to the activation energy for conductivity.

pH Dependency of Ni(OH)$_2$-based devices

The pH dependence of Ni(OH)$_2$ redox electrochemistry is well documented. Since the redox properties of Ni(OH)$_2$ modulate its conductivity, the resulting transistor properties are also pH-dependent.

Figure 9:
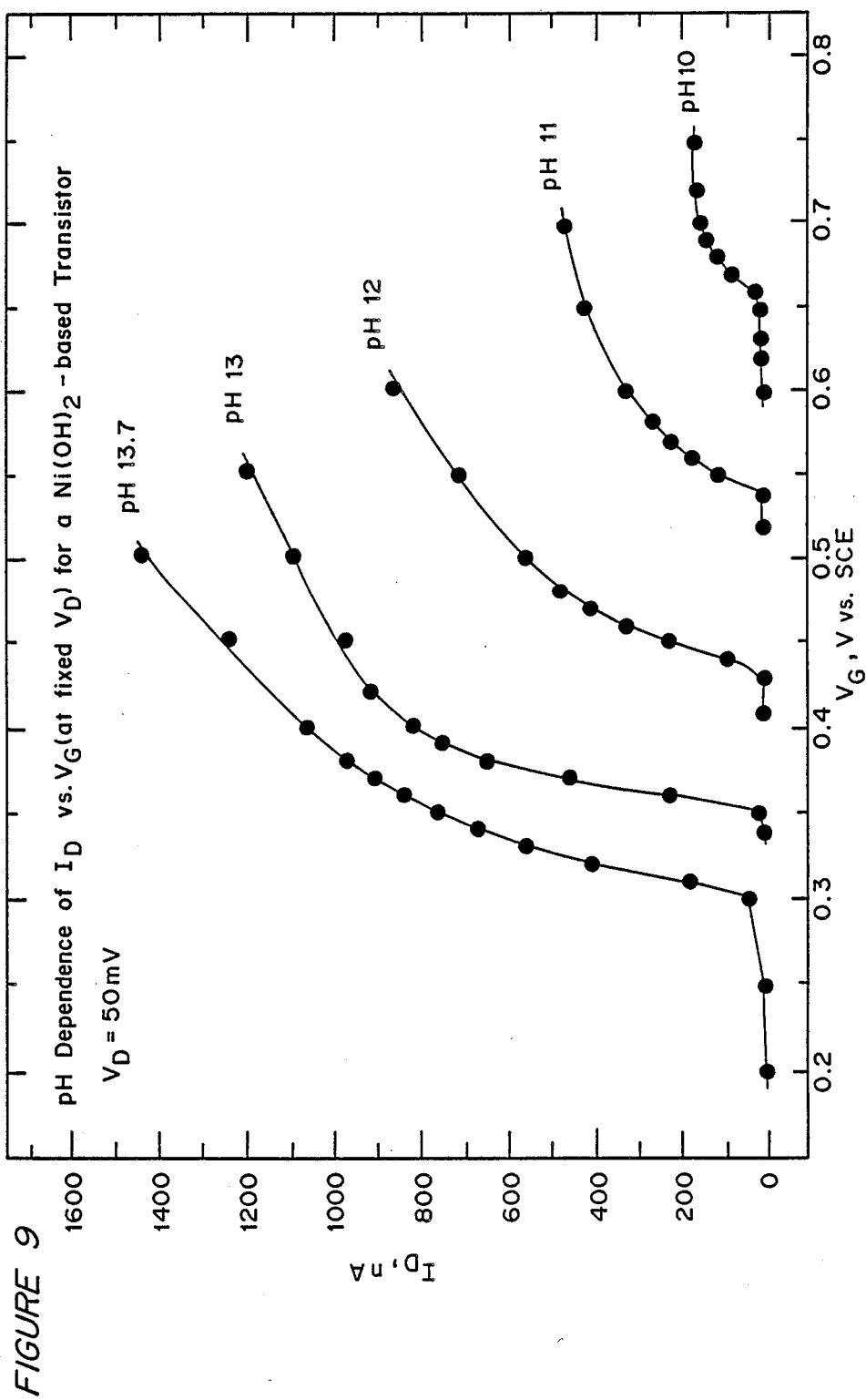
FIG. 9 is a plot showing the pH dependence of steady state $I_D$ vs. $V_G$ at fixed $V_D = 50$ mV for a $Ni(OH)_2$-based microelectrochemical transistor.

The effect of pH on the $I_D$-$V_G$ characteristics of the transistor (at fixed $V_D$) is illustrated by FIG. 9 that shows steady state $I_D$ at $V_D$=50 mV as a function of $V_G$ for Ni(OH)$_2$-based microelectrochemical transistors at different pH's. As the pH is lowered, the maximum value of $I_D$ steadily decreases. In addition, the turn-on $V_D$ shifts with pH. A pH-sensitive Ni(OH)$_2$-based microelectrochemical transistor operates by, at a fixed $V_G$ and $V_D$, exhibiting a change in $I_D$ as a function of pH. The pH regime in which a Ni(OH)$_2$-based device can operate is restricted to values of pH where reversible electrochemistry for Ni(OH)$_2$ is obtained, i.e., pH less than or equal to 10.

The maximum slope of the $I_d$-$V_G$ plots, which is closely related to the "transconductance" of solid state transistors, is 6 microamps/V change in $V_G$. It should be noted that the small maximum slope of the $I_D$-$V_G$ plot for Ni(OH)$_2$-based devices is not a hurdle to operation as a chemically sensitive transistor, since the $I_D$ output can always be further amplified.

As with WO$_3$-based devices, cyclic voltammetry at pH 14 of Ni(OH)$_2$-connected microelectrodes is independent of the presence of Li$^+$, Na$^+$, and K$^+$ cations and, further, there is no difference in the value of $I_D$ for Ni(OH)$_2$-based transistors exposed to these different media.

Characterization of RuO$_x$ films

The cyclic voltammetry of a ruthenium oxide film shows two waves. The first wave, centered at 0.0 V at pH 7.0, is broad and shows charging current positive of $E_{\frac{1}{2}}$, and is attributable to the Ru$^{IV/III}$ couple. The second Wave, which begins at ±0.35 V in pH 7.0 solution, is assigned to the Ru$^{VI/IV}$ couple At more positive potentials, this wave merges with the signal for O$_2$ evolution. Cycling RuO$_x$ to the potential of the second wave results in gradual film dissolution and loss of electroactivity. However, the film is remarkably stable as long as the electrode potential does not enter the second redox process: in one study, a RuO$_x$-derivatized electrode was cycled for 18 h between +0.3 and −0.5 V in pH 7.5 solution with less than 5% loss in the RuO$_x$ voltammogram. At potentials negative of the Ru$^{IV/III}$ wave, the RuO$_x$ film shows no faradaic activity until hydrogen evolution. No hydride oxidation signal is observed. Hydrogen evolution does not affect the Ru$^{IV/III}$ signal.

pH Dependency of RuO$_x$-based devices

Figure 10:
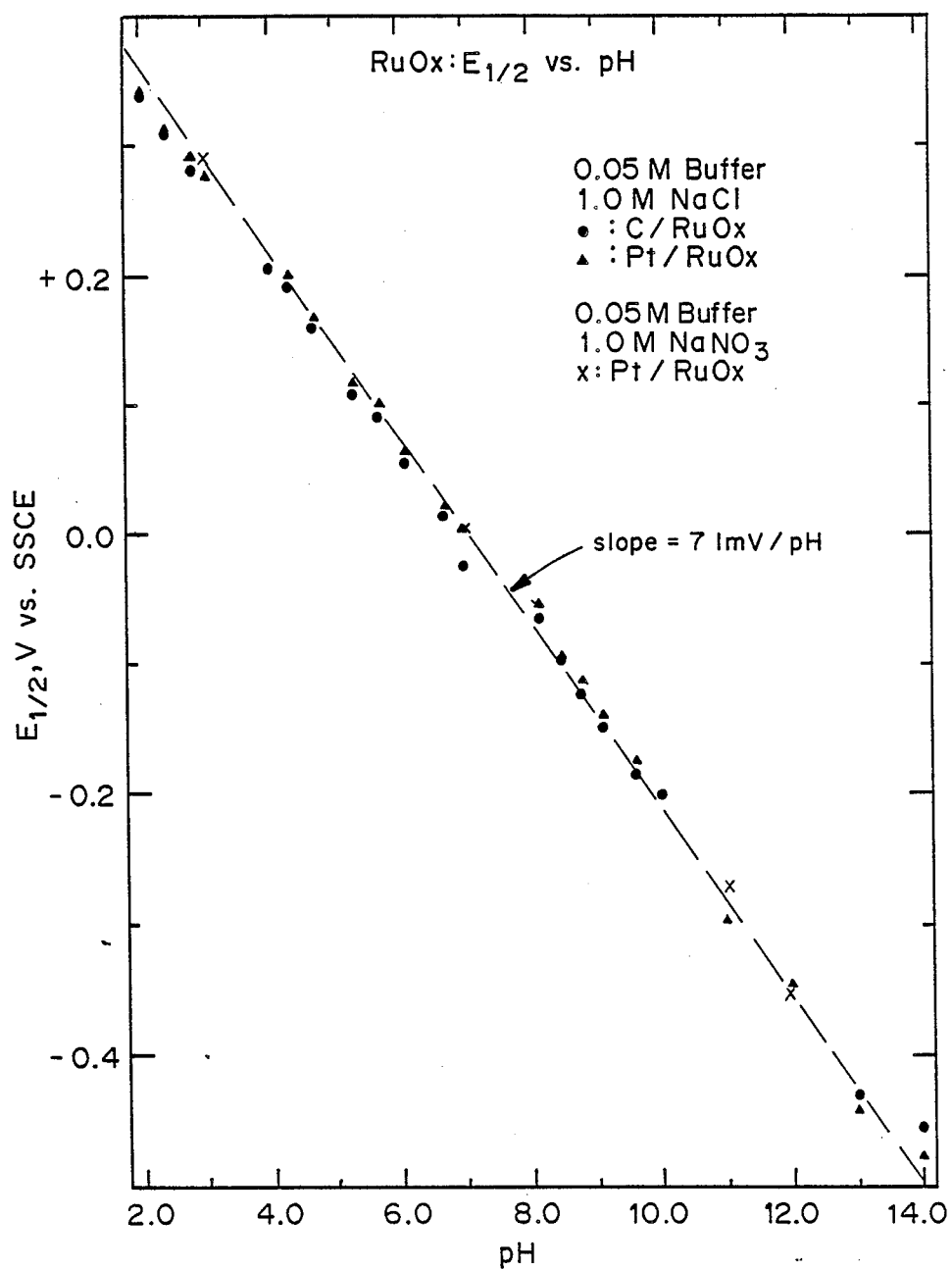
FIG. 10 is the half wave potential of $RuO_x$ as a function of pH where 0: $C/RuO_x$; Δ: $Pt/RuO_x$ (both in 0.05 M buffer/1.0 NaCl); X: $Pt/RuO_x$ in 0.05 M buffer/1.0 M $NaNO_3$. Extrapolation of the line yields $E_{\frac{1}{2}} = +0.05$ V vs. SSCE at pH=0.

RuO$_x$ electrochemistry is pH dependent and s "table over a wider pH range than other materials used to prepare microelectrochemical transistors. In unbuffered solutions the voltammetric waves become poorly defined. $E_{\frac{1}{2}}$ for the Ru$^{IV/III}$ wave varies 71 mV/pH unit from pH 2 to pH 14 as shown in FIG. 10. This relationship indicates that more than one proton is lost from the film for every electron that is withdrawn ($\approx$7 H$^+$ per 6e−). The pH dependence is similar for both NaCl and NaNO$_3$ supporting electrolytes. This effect is usually attributed to the acid-base properties of the oxides; for example, proton loss from coordinated water molecules may occur upon oxidation due to the higher positive charge on the central metal atoms.

Figure 11:
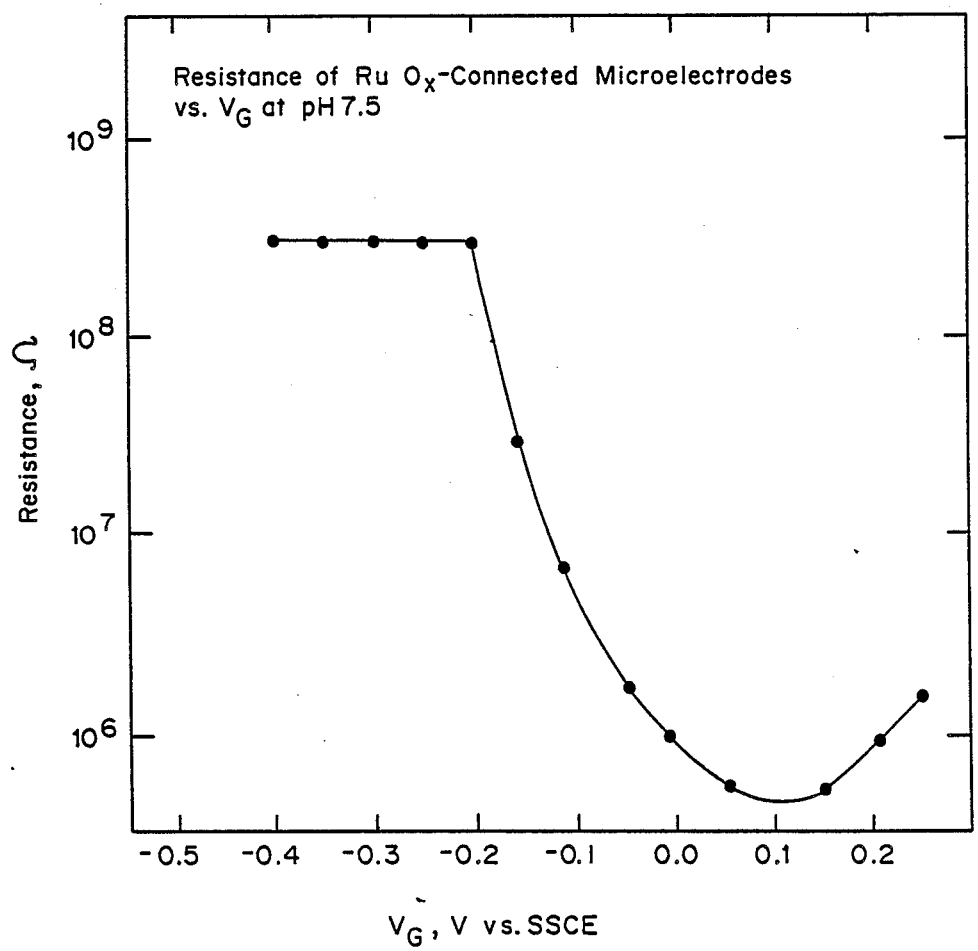
FIG. 11 is the resistance of $RuO_x$-connected microelectrodes as a function of $V_G$ at pH 7.5, as obtained by scanning one electrode at ±25 mV about $V_G$ at 50 mV/s.

An important property of microelectrode-based transistors is the resistance, as a function of $V_G$, between two microelectrodes connected by a redox-active material. FIG. 11 illustrates this for RuO$_x$-connected microelectrodes at pH 7.5. Like previously characterized microelectrochemical devices, the change in resistance of RuO$_x$ is associated with injection or withdrawal of charge in an electrochemical redox process. Measurement of the resistance entails bringing adjacent, RuO$_x$-connected electrodes to a given $V_G$, waiting until redox equilibrium is established, and slowly scanning the potential of one microelectrode by a small amount around $V_G$, While holding the adjacent electrode at $V_G$. With RuO$_x$-connected microelectrodes, measurements were made approximately 5 minutes after moving to a new $V_G$. Changes in resistance are observed by varying $V_G$ through the region where redox processes occur. The current passing between the electrodes was measured and related to the resistance by Ohm's law.

4 The data in FIG. 11 show that the resistance of RuO$_x$-connected microelectrodes varies by about three orders of magnitude; from $\approx$10$^9$ ohms to $\approx$10$^6$ ohms, as $V_G$ is varied from −0.4 to 0.1 V. The resistance minimum seen for RuO$_x$-connected microelectrodes is PH-dependent and occurs $\approx$100 mV positive of $E_{\frac{1}{2}}$ for the pH of the electrolyte.

Figure 12:
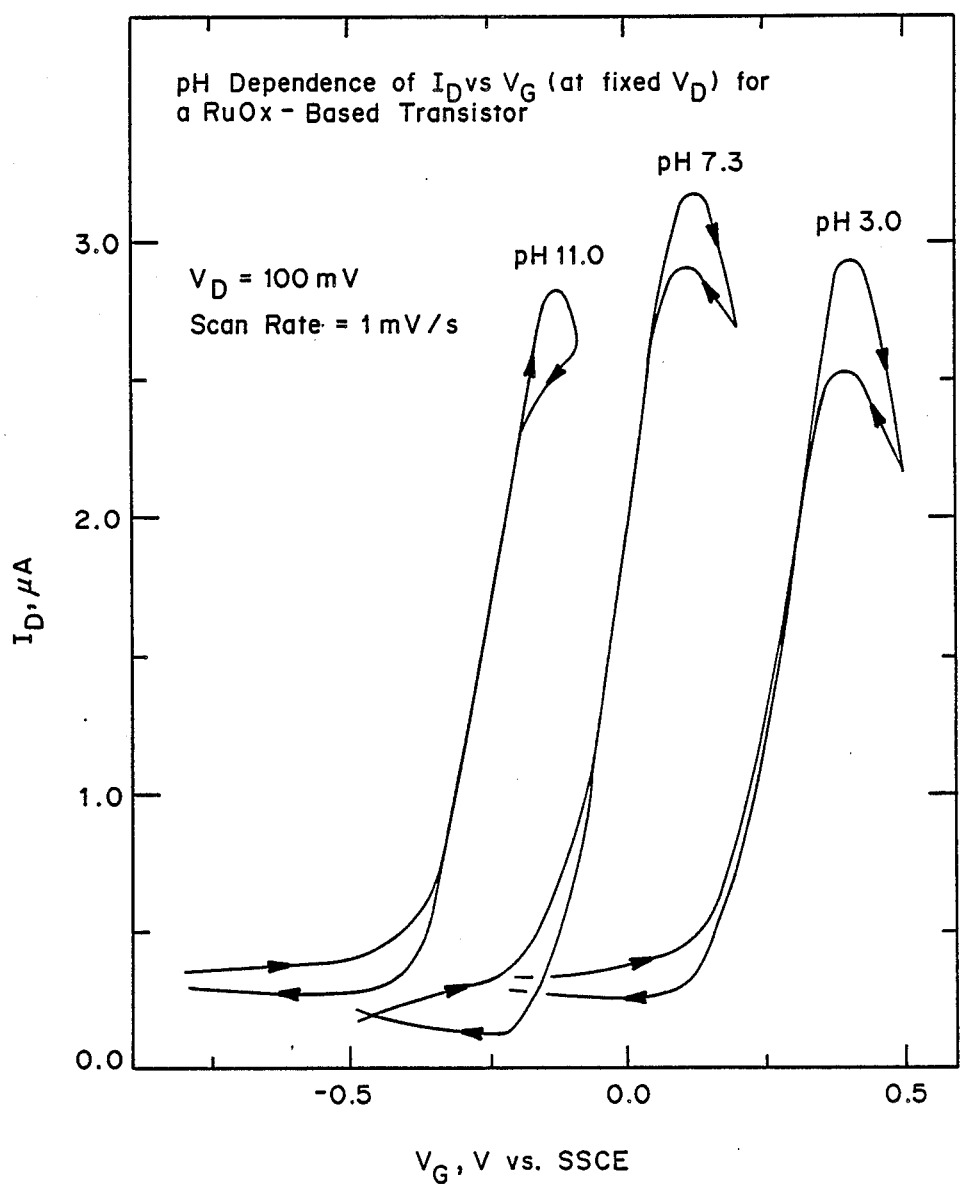
FIG. 12 is a plot of the pH dependence of steady state $I_D$ (μA) vs. $V_G$ (at fixed $V_D=100$ mV) for a RuO$_x$-based microelectrochemical transistor.

FIG. 12 illustrates the steady state current voltage charcteristics of a RuO$_x$-based microelectrochemical transistor. $V_D$ is fixed at 100 mV and $V_G$ is slowly scanned across the potential regime of interest in solutions having a pH of 3.0, 7.3, and 11.0. Since $I_D$ depends on the charge transport properties of RuO$_x$, these steady state data agree with the cyclic voltammetry results on macroscopic electrodes. Due to the low conductivity of RuO$_x$, the maximum scan rate is limited. At scan rates of less than about 50 mV/s, electrons cannot completely diffuse across the 1.4 μm gap between electrodes and the $I_D$/$V_G$ looks like a conventional cyclic voltammogram. Smaller separations are therefore required for use with higher scan rates.

Figure 13:
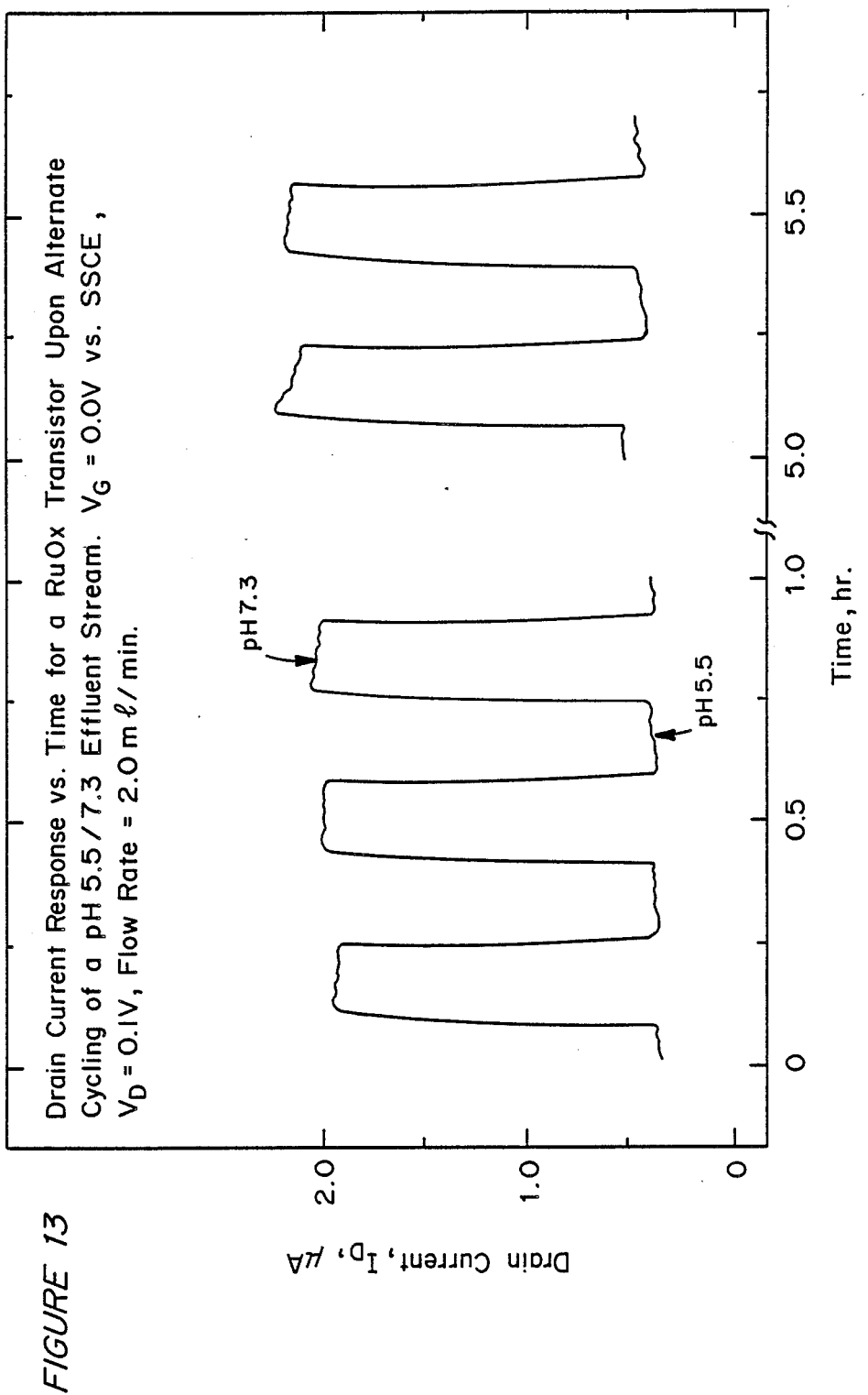
FIG. 13 is a plot of $I_D$ vs. time (hr) for a RuO$_x$-based microelectrochemical transistor as the pH of a continuously flowing stream is varied from 5.5 to 7.3 at $V_G=0.0$ V vs. SSCE and $V_D=100$ mV.

The pH-dependent nature of the $I_D$/$V_G$ data serves as the basis for a pH sensor, as shown in FIG. 13. A RuO$_x$ transistor was placed in the effluent stream of HPLC and the pH of the stream varied from 5.5 to 7.3. $V_G$ was fixed at 0.0 V and $V_D$ was set at 100 mV. At this $V_G$, RuO$_x$ is poorly conducting in pH 5.5 solution. It is significantly more conducting in pH 7.3 solution, as shown by a comparison of the $I_D$. The RuO$_x$-based device is durable and maintains nearly constant $I_D$ values over five h of operation.

Prussian Blue-based Microelectrochemical Devices

Figure 14:
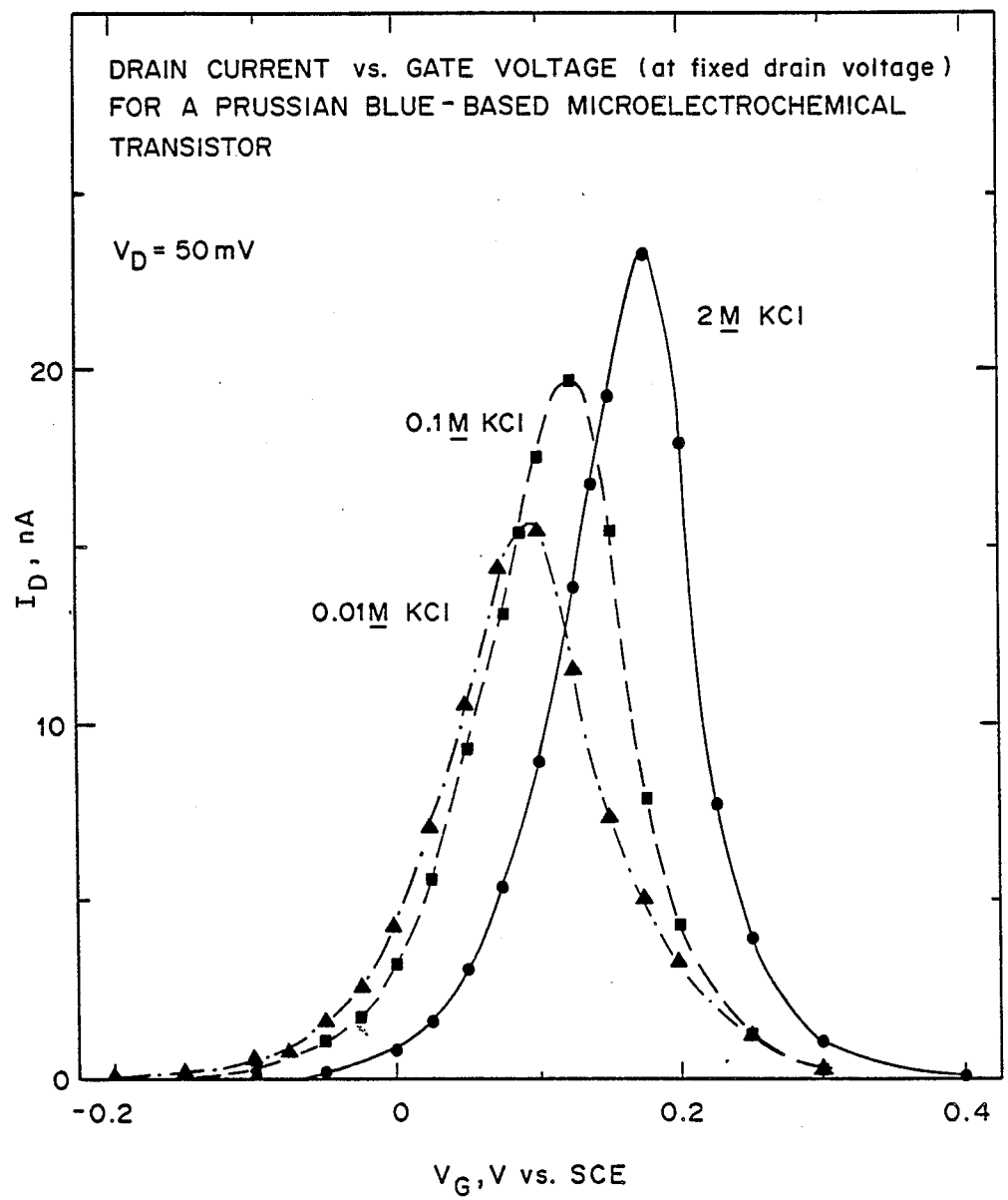
FIG. 14 is a plot of $I_D$ (nA) vs. $V_G$ (V vs. SCE) at a fixed $V_D=50$ mV as a function of salt concentration, 0.01 M KCl, 0.1 M KCl, and 2 M KCl, for a Prussian Blue based microelectrochemical device.
Figure 15:
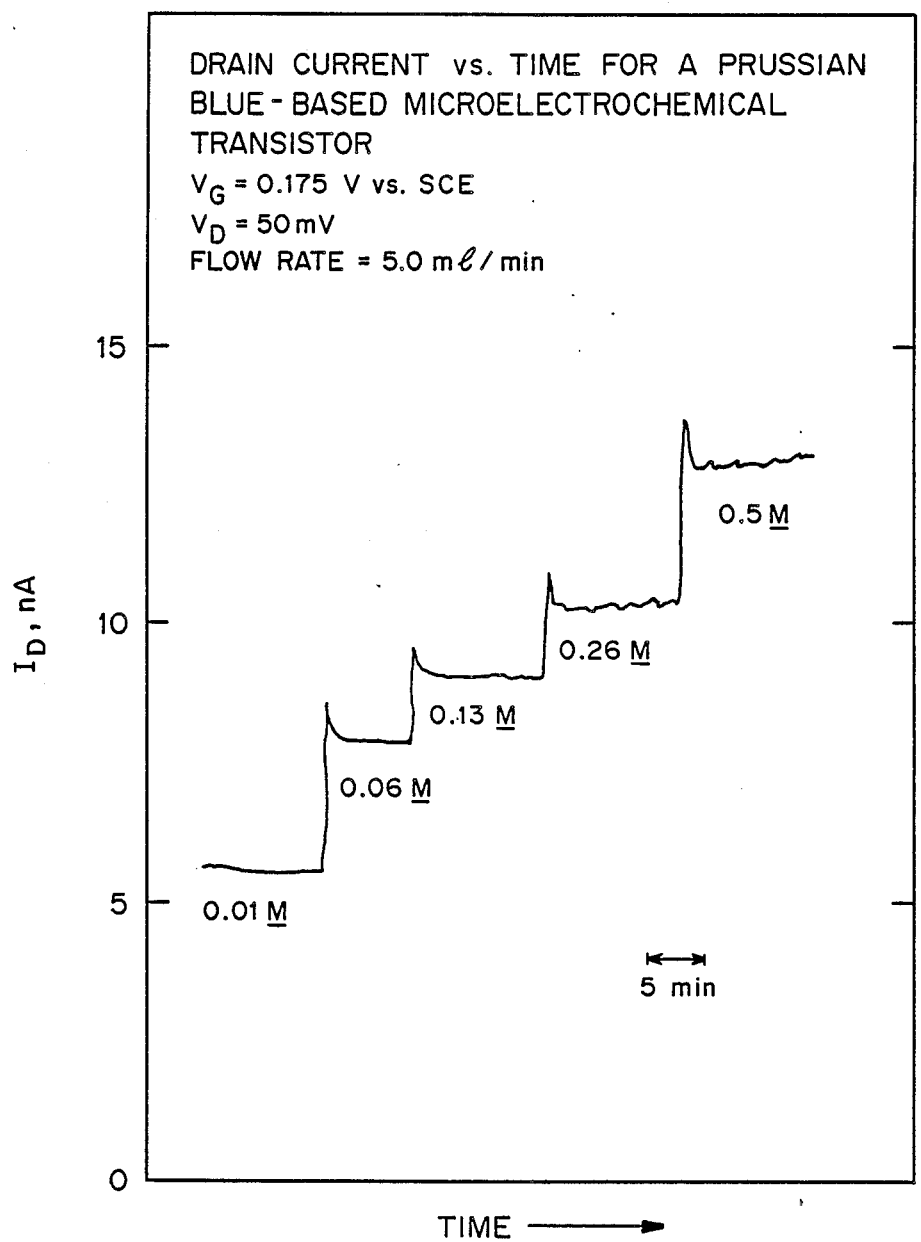
FIG. 15 is a plot of $I_D$ (nA) vs time at $V_G=0.175$ V vs. SCE, $V_D=50$ mV, in an HPLC system at at flow rate of 5.0 ml/min, as a function of concentration: 0.01 M, 0.06 M, 0.13 M, 0.26 M, and 0.5 M.
Figure 16:
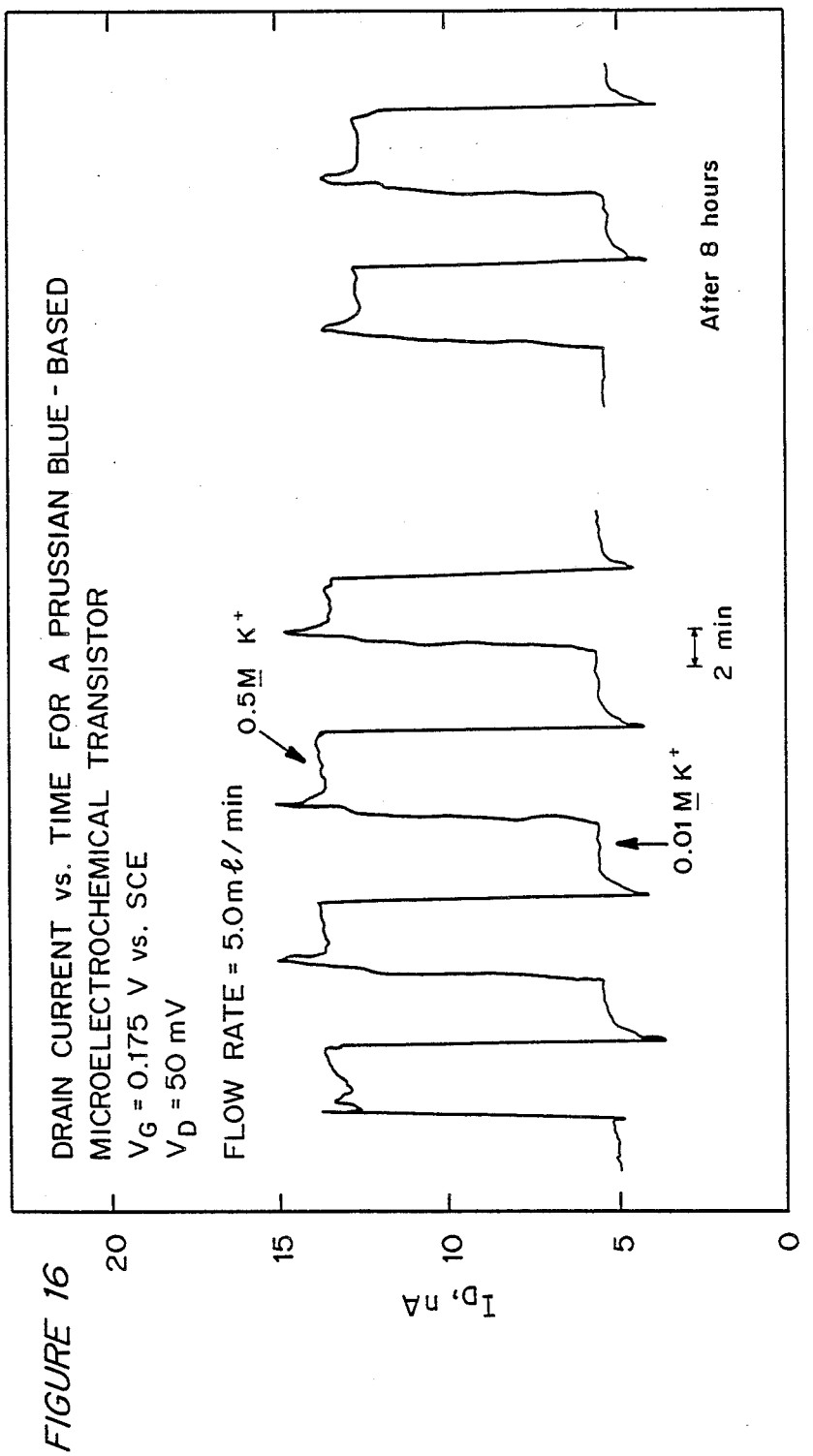
FIG. 16 is a plot of $I_D$ (nA) vs. time for a Prussian Blue based microelectrochemical transistor at $V_G=0.175$ V vs. SCE and $V_D=50$ mV in an HPLC system at a flow rate of 5.0 ml/min, comparing the effect of injections of 0.01 M K$^+$ and 0.5 M K$^+$.

As examples of other microelectrochemical devices constructed by overlaying a metal ion-based redox active material on microelectrodes, transistors were assembled according to the previously described methods using Prussian Blue as the redox active material. FIG. 14 graphs the $I_D$ vs $V_G$ at a fixed drain voltage (50 mV) for a Prussian Blue-based microelectrochemical transistor as a function of salt concentration, 0.01 M KCl, 0.1 M KCl, and 2 M KCl. The sensitivity and stability of this response is further shown by FIGS. 15 and 16. It is clear that this represents a second class of redox active materials useful as highly sensitive, specific chemical sensors according to the present invention.

Modifications and variations of the present invention, microelectrochemical devices based on metal ion redox active materials such as transition metal oxides and Prussian blue, will be apparent to those skilled in the art from the foregoing detailed description of the invention. Such modifications and variations are intended to come within the scope of the appended claims.

I claim:

1. A microelectrochemical device comprising at least two electrically conductive electrodes, separated by less than two microns, on an insulating substrate overlaid with a metal ion-based redox active material.

2. The device of claim 1 wherein said redox active material is selected from the group consisting of oxides and mixed oxides of W, Ni, Co, Rh, Ir, Nb, Mo, and V and Prussian Blue.

3. The device of claim I further comprising an electrolyte solution.

4. The device of claim 1 further comprising at least one electroactive polymer, wherein said device is responsive to a signal that changes the state of charge of the electroactive polymer which results in a net change in the concentration of ionic species in said polymer.

5. The device of claim 4 wherein said polymer is polymerized from monomers selected from the group consisting of N-methylpyrrole, aniline, thiophene, 3-methylthiophene, 3,4-dimethylthiophene, vinylferrocene, styrene, nitrostyrene, viologens, vinyl-pyridine, vinyl-2,2'-bipyridine, vinylrubrene, quinone-based compounds, and derivatives thereof.

6. The device of claim 1 wherein said redox active material is derivatized with a material selected from the group consisting of metals, enzymes, and ionophores.

7. The device of claim 1 Wherein said device responds to an electrical signal.

8. The device of claim 1 wherein said device responds to a chemical signal.

9. The device of claim wherein said device functions analogously to a transistor.

10. The device of claim 9 wherein said device is a pH-sensitive p-n-p transistor prepared by derivatizing adjacent microelectrodes with poly(3-methylthiophene), a transition metal oxide, and poly(3-methylthiophene).

11. The device of claim 1 wherein said device exhibits rectification.

12. The device of claim 1 wherein said device functions analogously to a diode.

13. The device of claim 12 wherein said device is a pH sensitive transition metal oxide/electroactive redox polymer diode.

14. A method for sensing a chemical signal comprising
    providing a device constructed from at least two microelectrodes, separated by less than two microns, on an insulating substrate, overlaid with a metal ion-based redox active material whose conductivity changes as a function of the movement of ions into or out of the material, and
    detecting signals by measuring changes in conductivity of said metal ion based redox active material.

15. The method of claim 14 for monitoring pH further comprising selecting the redox active material for stability within the pH range to be monitored.

16. The method of claim 15 further comprising maintaining a set $V_D$ and $V_G$ across the microelectrodes and determining the pH from variations in $I_D$.

17. The method of claim 14 further comprising selecting said redox material from the group consisting of transition metal oxides and mixed oxides and Prussian Blue.

18. The method of claim 14 further comprising derivatizing the material with an enzyme reacting with a chemical substance to be measured wherein the reaction of the enzyme and chemical substance causes a change in the oxidation/reduction state of the metal oxide.

19. The method of claim 18 further comprising measuring the current passing between adjacent microelectrodes as a function of the reaction of the enzyme with the substance to be measured, taking the derivative of the measured current to the rate of reduction of the metal oxide, and determining the concentration of the substance to be measured by calculating the enzyme kinetics.

20. The method of claim 14 wherein the signal is determined by a change in the measured current through the metal oxide as a function of the oxidation/reduction of the oxide.

21. The method of claim 14 further comprising increasing the sensitivity of the device by decreasing the distance between the microelectrodes.

22. The method of claim 14 further comprising decreasing the response time of the device by decreasing the thickness of the metal oxide on the microelectrodes.

* * * * *